US010741273B1

(12) United States Patent
Kumar

(10) Patent No.: US 10,741,273 B1
(45) Date of Patent: Aug. 11, 2020

(54) USER FRIENDLY MEDICAL RECORDS SYSTEMS, APPARATUSES AND METHODS

(71) Applicant: OHUM Healthcare Solutions Inc., Naperville, IL (US)

(72) Inventor: Udai Kumar, Naperville, IL (US)

(73) Assignee: OHUM Healthcare Solutions Inc., Naperville, IL (US)

( * ) Notice: Subject to any disclaimer, the term of this patent is extended or adjusted under 35 U.S.C. 154(b) by 902 days.

(21) Appl. No.: 14/800,318

(22) Filed: Jul. 15, 2015

(51) Int. Cl.
*G16H 10/60* (2018.01)
*G16H 80/00* (2018.01)
*G16H 50/30* (2018.01)
*G16H 10/65* (2018.01)

(52) U.S. Cl.
CPC ............ *G16H 10/65* (2018.01); *G16H 10/60* (2018.01); *G16H 80/00* (2018.01); *G16H 50/30* (2018.01)

(58) Field of Classification Search
CPC ........ G16H 10/65; G16H 10/00; G16H 10/20; G16H 10/40; G16H 10/60; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00; G16H 50/30; G06F 19/323; G06Q 50/22
USPC ........................................................ 705/2–3
See application file for complete search history.

(56) References Cited

U.S. PATENT DOCUMENTS

| | | | |
|---|---|---|---|
| 6,208,974 B1 * | 3/2001 | Campbell | G06F 19/328 705/3 |
| 2002/0065686 A1 * | 5/2002 | Monteleone | G06F 19/3418 705/3 |
| 2007/0165049 A1 * | 7/2007 | Murawski | G06Q 10/00 345/619 |
| 2008/0258913 A1 * | 10/2008 | Busey | G08B 21/0415 340/540 |
| 2009/0076848 A1 * | 3/2009 | Bulat | A61B 5/0002 705/2 |
| 2011/0029929 A1 * | 2/2011 | Clauson | G06F 3/0482 715/843 |

(Continued)

OTHER PUBLICATIONS

Orion Health, (http://www.orionhealth.com) (Downloaded Jun. 13, 2019), "Solutions for Healthcare Providers Deliver the perfect care for each individual across the community", 9 pages.

*Primary Examiner* — Eliza A Lam
(74) *Attorney, Agent, or Firm* — Banner & Witcoff, Ltd.

(57) ABSTRACT

Methods, systems, computer-readable media, and apparatuses for providing a personalized manager for use with an electronic health record system such as VistA. A mobile device may work in tandem with backend services to provide a tile-based user interface customized to each physician. The mobile device may, based on physician input relating to a patient, dynamically reorder tiles of the tile-based user interface. Further, the physician may specify one or more conditions that when satisfied by a patient trigger an alert to medical professionals to begin a preventative treatment so that a particular patient ailment does not occur. Backend services may store information customized by the physician for use in generating treatment recommendations.

19 Claims, 17 Drawing Sheets

(56) References Cited

U.S. PATENT DOCUMENTS

| | | | |
|---|---|---|---|
| 2014/0340219 A1* | 11/2014 | Russell | G08B 21/043 340/539.12 |
| 2014/0368547 A1* | 12/2014 | Elings | G06T 3/60 345/659 |
| 2015/0012298 A1* | 1/2015 | Ash | G06F 19/345 705/3 |

* cited by examiner

USER FRIENDLY MEDICAL RECORDS SYSTEMS, APPARATUSES AND METHODS

FIELD

Aspects of the disclosure relate to computer hardware and software. In particular, one or more aspects of the disclosure generally relate to computer hardware and software for providing user friendly medical records software for use by physicians and other medical professionals thereby resulting in better patient care. The computer hardware and software may alert appropriate medical professionals of an impending medical emergency for a particular patient.

BACKGROUND

Veterans Health Information Systems and Technology Architecture (VistA) is an information system used by the United States Department of Veterans Affairs (VA). Since most physicians in the United States have a rotation and/or otherwise practiced medicine at the VA, most of the physicians in the United States are familiar with and/or otherwise know how to use VistA. VistA has a computerized patient record system (CRPS) that provides an archaic Windows-style user interface similar to that found in Windows operating systems from the early 1990s. Further, the user interface often takes as many 8-12 steps (e.g., 8-12 separate user selections in various menus and submenus) for the physician to access and view a particular piece of information. Thus, VistA requires the physician to search through menus upon menus of the user interface for the physician to find information, which needlessly wastes the physician's time. Physicians who are not well versed in the user interface may experience a vast amount of frustration when they are unable to find needed information or only able to find the needed information after wasting the physician's precious time. Such frustrations and lack of efficiency have led many physicians (including physicians who are well versed in VistA) to refrain and/or otherwise abandon use of the system whenever possible thereby weakening the data integrity of the system.

Additionally, the medical field is having a hard time ensuring industry standards are followed as the VistA system has no ability to track that a procedure was followed in a particular order in response to detecting a particular patient symptom. Further, the medical industry does not have unified procedures for hospitals to enforce industry standards. When a physician does not follow industry standards, preventable, irreversible and potentially deadly mistakes in patient care occur.

Further, while a patient in a hospital room may be monitored by various different monitoring devices (e.g., heart rate monitor, breathing monitor, etc.). Such monitors do not predict a potential future medical condition of the patient. As a result, many medication conditions are only diagnosed after they occur.

Accordingly, there is a persistent need to create a user-friendly system for physicians to access and manipulate medical records, as well as helps ensure industry standards are followed and aid in prediction and prevention of future medical conditions of the patient.

BRIEF SUMMARY

The following presents a simplified summary of various aspects described herein. This summary is not an extensive overview, and is not intended to identify key or critical elements or to delineate the scope of the claims. The following summary merely presents some concepts in a simplified form as an introductory prelude to the more detailed description provided below.

Various aspects of the disclosure provide more efficient, effective, functional, and convenient ways of providing patient care. In particular, in one or more embodiments discussed in greater detail below, physician-customizable management functionalities are implemented, and/or used in a number of different ways to provide one or more of these and/or other advantages.

Methods, systems, computer-readable media, and apparatuses for providing more efficient and effective patient care. A user-friendly medical mobile app may work in tandem with backend services to enable a physician to view a single tile-based user interface in which the physician may view, add and edit information related to a patient. The tile-based user interface may be ordered and/or dynamically reordered based on preferences of the physician, the physician treatment history of patients with the same complaints or symptoms, etc. The tile-based user interface may enable to physician to quickly find and modify information without having to select multiple menus and sub-menus. The tile-based user interface may be personalized for the physician based on preferences (e.g., preferences of the particular physician, preferences of the hospital system for which the physician works, an administrator, or others). Further, the tile-based user interface may support gestures (e.g., touch-based gestures such as swiping two fingers in a particular direction, a long-hold on a displayed content item, etc.). The physician may efficiently perform various actions on displayed content items by performing one or more gestures on those displayed content items. As an example, one gesture may copy information in a tile, and another gesture may generate a billing report. The gestures may be consistent across the various tiles. The tile-based user interface may be displayed on a mobile device so that the physician can input medical information while the physician is moving around the hospital or while in front of the patient. The tile-based user interface may include a significant information icon (e.g., button), which when selected by the physician may display abnormal patient conditions that is relevant to the physician.

Backend services may receive information entered by the physician (e.g., dosage, how many medications he orders, diagnosis of patient, etc.), big data factors, and other physician preferences, and use this information to determine recommendations for the physician (e.g., predict and recommend medications the physician prefers). Backend services may then transmit the recommendations to the user-friendly medical app for display to the physician.

The physician may specify one or more conditions that when met by the patient trigger an alert that is sent to one or more specified persons. The one or more conditions may be specific to the patient's conditions and may be indicative that the patient is at risk or likely to acquire a medical condition such as pneumonia. The alert may be sent to the persons specified by the physician so that those persons can take preventative measure to prevent the patient from acquiring the medical condition.

In one or more arrangements, one or more medical professional may author a note for a patient on a periodic basis (e.g., daily, weekly, and/or yearly), which they may submit using natural language input (e.g., free text) via a user-friendly medical app installed on a portable device. The natural language inputs may include patient assessment, initial diagnosis, etc. Data may be captured from the natural language by either the user-friendly medical app itself or a backend service that received the note from the user-friendly medical app. The data may be captured by populating disease-specific templates (stored at the portable device and/or a backend service). At the end of the particular time period (e.g., at the end of each day, month and/or year) a medical professional responsible for the patient's care may sign the note on behalf of the one or more medical professionals to thereby lock the note. Once locked, the note may not be altered. For instance, the user-friendly medical app and/or the backend service may prevent other users from modifying the note. Use of this note taking feature of the user-friendly medical app may eliminate redundant statements and miscommunications among the one or more professionals. Additionally, once the note is signed, the user friendly medical app and/or backend services may codify the data of the note into one or more clinical codes representative of clinical terminology (e.g., Systematized Nomenclature of Medicine—Clinical Terms).

Further, the user-friendly medical app and/or the backend services may store a mapping of the clinical codes to one or more suggested billing codes (e.g., ICD-10 billing codes) and use the mapping to identify suggested billing codes based on the clinical codes. Using a rules engine, the user-friendly medical app itself and/or the backend services may cause the user-friendly medical app to display requests for additional information to justify one or more of the billing codes based on one or more rule of the rules engine to ensure that there is sufficient information to justify a particular billing code. The justification may include diagnoses and/or treatment of the patient. As a result of use of the mapping, medical professionals may focus their attention on clinical codes rather than on billing codes.

In some embodiments, a system may include a backend computing device configured to store one or more physician-specific preferences. The system may also include a mobile device communicatively coupled to the backend computing and an electronic health record information system. The mobile device may include a processor and computer-readable medium storing instructions that, when executed by the processor, cause the mobile device to perform a number of steps. For instance, the mobile device may display a tile-based user interface, which may be unified and streamlined into a single screen. The tile-based user interface may be customized for a first physician based on the one or more physician-specific preferences, and may comprise, for a patient, a documentation tile, a diagnosis tile, a treatment plan tile, a lab results tile, a medication or prescription tile, and a significant information icon. The mobile device may receive a user selection to activate the significant information icon. The mobile device may display abnormal lab results of the patient that are significant for the first physician based on a task to be performed by the first physician. The abnormal lab results might not be significant to a second physician to perform a different task on the patient.

In some embodiments, an apparatus may include a processor and a computer-readable memory coupled to the processor. The computer-readable memory may store instructions that, when executed by the processor, cause the apparatus to perform a number of steps. For instance, the apparatus may display a tile-based user interface customized for a first physician. The apparatus may receive input from the first physician indicative of a first diagnosis of a patient. The apparatus may determine that the first diagnosis is associated with a patient standard of care specifying an order of user inputs. The apparatus may permit further input from the first physician that is in accordance with the patient standard of care specifying the order of user inputs. The apparatus may block other input from the first physician that is not in accordance with the patient standard of care specifying the order of user inputs.

These features, along with many others, are discussed in greater detail below.

BRIEF DESCRIPTION OF THE DRAWINGS

The present disclosure is illustrated by way of example and not limited in the accompanying drawings in which like reference numerals indicate similar elements and in which:

FIGS. 6 and 7 depict various illustrative views of a tile-based user interface in accordance with one or more illustrative aspects discussed herein.

DETAILED DESCRIPTION

In the following description of the various embodiments, reference is made to the accompanying drawings, which form a part hereof, and in which is shown by way of illustration various embodiments in which the user-friendly medical records solution may be practiced. It is to be understood that other embodiments may be utilized and structural and functional modifications may be made without departing from the scope of aspects discussed herein. The user-friendly medical records system is capable of other embodiments and of being practiced or being carried out in various ways.

Also, it is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof. The use of the terms "mounted," "connected," "coupled," "positioned," "engaged" and similar terms, is meant to include both direct and indirect mounting, connecting, coupling, positioning and engaging.

One or more aspects describes herein provide medical professionals (e.g., physicians, nurses) access to an analysis of a patient's medical record on a single tile-based user interface for manipulation. The access may be provided through the form of an application such as a mobile application for use on a tablet computer. The application may coordinate with backend services including, for example, patient data, medical knowledge systems, billing systems, documentation systems, administrative systems, prescription-ordering systems, or the like. By having a single one-stop user interface, the application enables medical professionals to quickly and efficiently access particular information (e.g., particular patient information, medical knowledge, physician notes, etc.) in one step (e.g., a single touch-based selection by the medical professional).

Other features and advantages of the disclosure will be apparent from the additional description provided herein.

Figure 1:
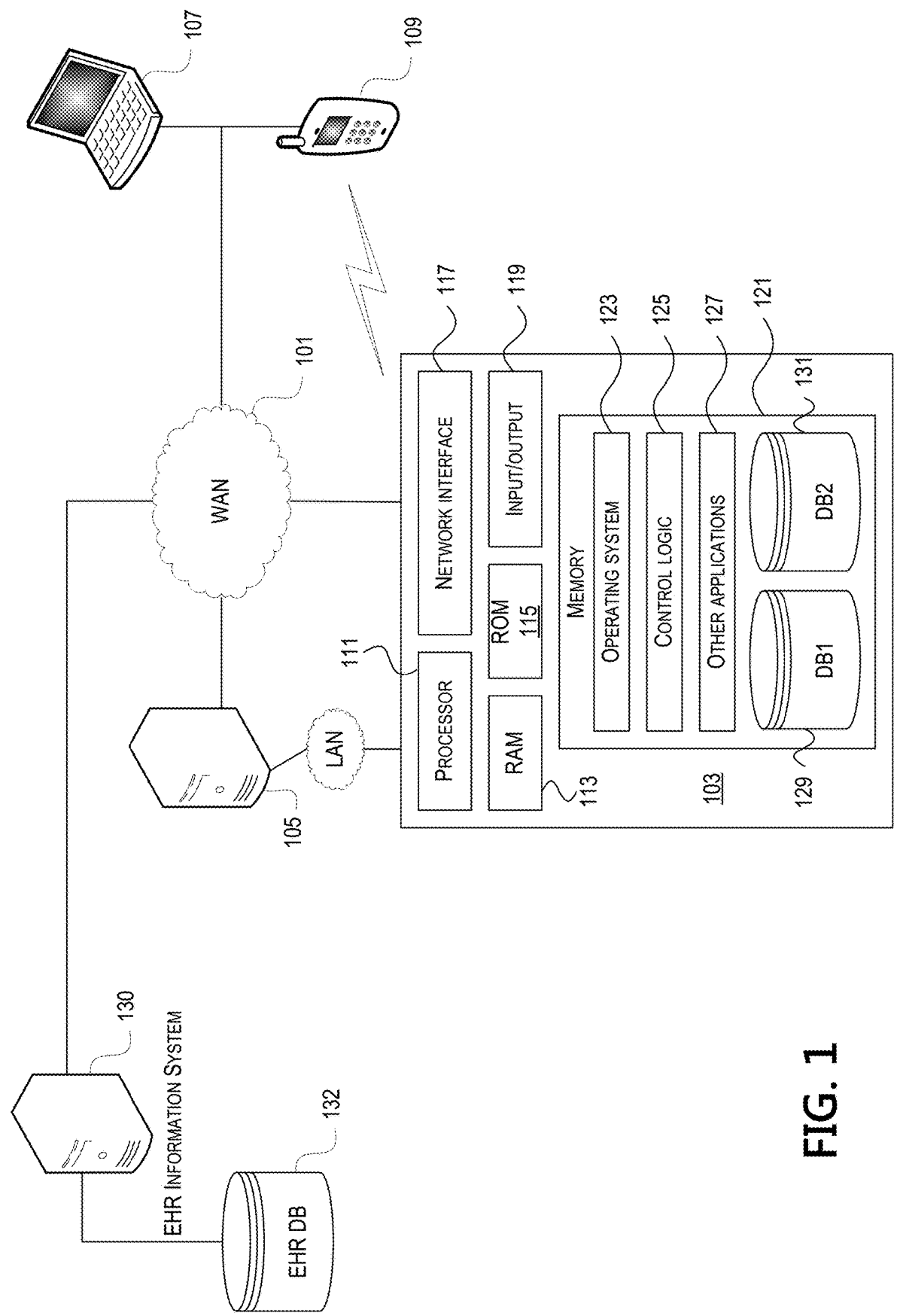
FIG. 1 depicts an illustrative network architecture and data processing device that may be used to implement one or more illustrative aspects described herein.

FIG. 1 illustrates one example of a network architecture and data processing device that may be used to implement one or more illustrative aspects described herein. Various network nodes 103, 105, 107, 109, 130 may be interconnected via a wide area network (WAN) 101, such as the Internet. Other networks may also or alternatively be used, including private intranets, corporate networks, LANs, wireless networks, personal networks (PAN), and the like. Network 101 is for illustration purposes and may be replaced with fewer or additional computer networks. A local area network (LAN) may have one or more of any known LAN topology and may use one or more of a variety of different protocols, such as Ethernet. Devices 103, 105, 107, 109 and other devices (not shown) may be connected to one or more of the networks via twisted pair wires, coaxial cable, fiber optics, radio waves or other communication media. For example, as shown, device 109 may be connected to various network nodes 103, 105, 107, and 130 via a radio frequency, such as, for example, a cellular communications signal.

The term "network" as used herein and depicted in the drawings refers not only to systems in which remote storage devices are coupled together via one or more communication paths, but also to stand-alone devices that may be coupled, from time to time, to such systems that have storage capability. Consequently, the term "network" includes not only a "physical network" but also a "content network," which is comprised of the data—attributable to a single entity—which resides across all physical networks.

The components may include data server 103, web server 105, client computer 107, and a mobile device 109. Data server 103 provides overall access, control and administration of databases and control software for performing one or more illustrative aspects described herein. Data server 103 may be connected to web server 105 through which users interact with and obtain data as requested. Alternatively, data server 103 may act as a web server itself and be directly connected to the Internet. Data server 103 may be connected to web server 105 through the network 101 (e.g., the Internet), via direct or indirect connection, or via some other network. Users may interact with the data server 103 using remote computer 107, e.g., using a web browser to connect to the data server 103 via one or more externally exposed web sites hosted by web server 105. Client computer 107 may be used in concert with data server 103 to access data stored therein, or may be used for other purposes. For example, from client device 107 a user may access web server 105 using an Internet browser, as is known in the art, or by executing a software application that communicates with web server 105 and/or data server 103 over a computer network (such as the Internet). Similarly, mobile device 109 may be used in concert with data server 103 to access data stored therein, or may be used for other purposes. For example, from mobile device 109 a user may access web server 105 using an Internet browser or by executing a mobile application that communicates with the web server 105 and/or data server 103 over a network (e.g., Internet, cellular network, etc.).

The mobile device 109 (e.g., a smartphone, a tablet, a laptop, etc.) may include a variety of components. For example, mobile device 109 may include a visual display component (e.g., a touchscreen or other display screen) to present information to the user. Mobile device 109 may include a user input component (e.g., a touchscreen, physical buttons, keyboard, mouse, a stylus, or the like) to receive input from a user. Mobile device 109 may include a position determining component (e.g., a global positioning system) to determine the geographic location of mobile device 109. Mobile device 109 may include an optical detection component (e.g., a camera, scanner, etc.) to take a photographs, pictures, or images of physical objects. Mobile device 109 may include a wireless communication component (e.g., a cellular transceiver, a Wi-Fi transceiver, etc.) to communicate with remote devices (e.g., web server 105, data server 103, or the like).

Servers and applications may be combined on the same physical machines, and retain separate virtual or logical addresses, or may reside on separate physical machines. FIG. 1 illustrates just one example of a network architecture that may be used, and those of skill in the art will appreciate that the specific network architecture and data processing devices used may vary, and are secondary to the functionality that they provide, as further described herein. For example, services provided by web server 105 and data server 103 may be combined on a single server.

Each component 103, 105, 107, 109 may be any type of known computer, server, or data processing device. Data server 103, e.g., may include a processor 111 controlling overall operation of the rate server 103. Data server 103 may further include RAM 113, ROM 115, network interface 117, input/output interfaces 119 (e.g., keyboard, mouse, display, printer, etc.), and memory 121. I/O 119 may include a variety of interface units and drives for reading, writing, displaying, and/or printing data or files. Memory 121 may further store operating system software 123 for controlling overall operation of the data processing device 103, control logic 125 for instructing data server 103 to perform aspects as described herein, and other application software 127 providing secondary, support, and/or other functionality which may or may not be used in conjunction with aspects discussed herein. The control logic may also be referred to herein as the data server software 125. Functionality of the data server software may refer to operations or decisions made automatically based on rules coded into the control logic, made manually by a user providing input into the system, and/or a combination of automatic processing based on user input (e.g., queries, data updates, etc.).

Memory 121 may also store data used in performance of one or more aspects described herein, including a first database 129 and a second database 131. In some embodiments, the first database may include the second database (e.g., as a separate table, report, etc.). That is, the information can be stored in a single database, or separated into different logical, virtual, or physical databases, depending on system design. Devices 105, 107, 109 may have similar or different architecture as described with respect to device 103. Those of skill in the art will appreciate that the functionality of data processing device 103 (or device 105, 107, 109) as described herein may be spread across multiple data processing devices, for example, to distribute processing load across multiple computers, to segregate transactions based on geographic location, user access level, quality of service (QoS), etc.

Network node 130 may be a server or other processing device for providing medical data such as electronic health records (EHRs), medical knowledge, or the like for use by physicians or other medical professionals via devices 107, 109. Network node 130 may also be referred to herein as EHR information system 130. EHR information system 130 may include similar components to that of data server 103 and may communicate with various other nodes (e.g., data server 103). EHR information system 130 may execute multiple software modules for clinical care, billing functions, etc. Further, EHR information system 130 may store in one or more databases 132 electronic medical/health records (EHR) of patients for retrieval, access and updating by one or more computing devices discussed herein. An EHR of a patient may include the patient's medical history, family medical history, past and current prescribed medications, recent symptoms and corresponding notes and/or diagnoses by physicians or other medical professionals, lab test results, or other information typically found in medical records. EHR information system 130 may be, in one illustrative example, the Veterans Health Information Systems and Technology Architecture (VistA) used by the United States Department of Veterans Affairs (VA) and used by over half of all physicians in the United States. Clinical, financial, administrative, and patient portal functions of EHR information system 130 may include the same as those found in the VistA system.

EHR information system 130 may also store in, retrieve from, and manipulate clinical data in EHR database 132. Clinical data may include EHRs, administrative data, disease registries, health surveys, clinical trials data, demographic information, laboratory tests, insurance, prescription drugs, treatments, or the like. Following the above VistA example, EHR database 132 may be a Massachusetts General Hospital Utility Multi-Programming System (MUMPS) database. MUMPS database is a schema-less key-valued database used by the VA in conjunction with the VistA system. MUMPS programming language enable access to databases via variables rather than queries. In some embodiments, EHR information system 130 and EHR database 132 may be associated with an entity different an entity associated with data server 103 or devices 107, 109.

One or more aspects of the user-friendly medical records system may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a hard disk, optical disk, removable storage media, solid state memory, RAM, etc. As will be appreciated by one of skill in the art, the functionality of the program modules may be combined or distributed as desired in various embodiments. In addition, the functionality may be embodied in whole or in part in firmware or hardware equivalents such as integrated circuits, field programmable gate arrays (FPGA), and the like. Particular data structures may be used to more effectively implement one or more aspects discussed herein, and such data structures are contemplated within the scope of computer executable instructions and computer-usable data described herein.

The user-friendly medical records system may be implemented using the network architecture described in FIG. 1. For example, the user-friendly medical records system may be implemented via one or more of the data server 103, the web server 105, the client computer 107, and/or mobile device 109.

Figure 2:
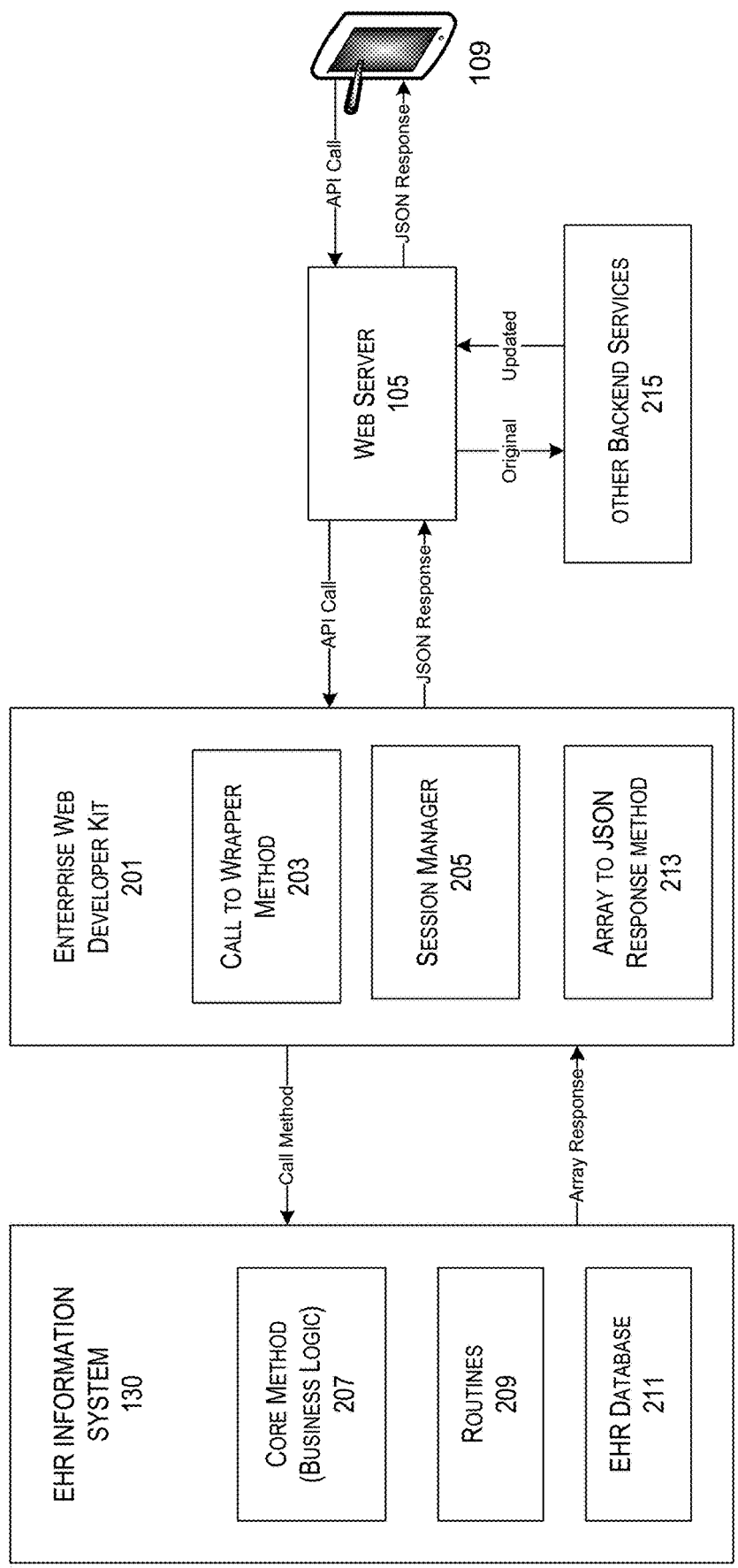
FIG. 2 illustrates an illustrative architecture demonstrating a message flow between a mobile device and various backend services in accordance with one or more illustrative aspects discussed herein.

FIG. 2 illustrates an illustrative architecture 200 demonstrating a message flow between mobile device 109 and various backend services in accordance with one or more illustrative aspects discussed herein. Mobile device 109 (e.g., a tablet or smartphone) may have a user-friendly medical app installed thereon for use by medical professionals. For instance, a physician while in the presence of a patient may, via the user-friendly medical app, access that patient's medical records, medical knowledge relevant to the patient's symptoms, and/or medical analysis of the patient. As an example, the physician upon seeing the patient may wish to obtain the patient's current medical record. In such an example, the physician may input a patient identifier (e.g., patient ID, patient's name, patient-specific bar code, or the like) for example by touching an onscreen keyboard of mobile device 109, by speaking the patient identifier to a microphone of mobile device 109, or by scanning the patient identifier (e.g., bar code, quick response code, radio frequency identifier tag, etc.) using a scanning device (e.g., camera, radio frequency reader, etc.).

An app connectivity layer of mobile device 109 may use a shared protocol to format the physician's input (e.g., the request for the patient's medical record). The app connectivity layer may format the physician's' input into an application programming interface (API) call and transmit the API call to webserver 105 (e.g., executing Apache or another open-source protocol), which may relay the API call to an enterprise web developer kit (EWD) 201 residing either at its own computing device, the webserver 105, or the EHR information system 130. EWD 201 may use session manage 205 to manage multiple user sessions where each session may be specific to a particular physician and associated with a particular session identifier (ID). The session ID may also be used to identify the browser or particular instance of the user-friendly mobile app from which the API call originated. EWD 201 may also include have session timeout functionality. For instance, if the physician and/or the EHR information system 130 fails to provide a response within a maximum timeout time period (e.g., is inactive for the time period), EWD 201 may terminate the user's session.

EWD 201 may act as a gateway between webserver 105 and EHR information system 130 by formatting communications between webserver 105 and EHR information system 130. As an example, EWD 201 may format the API call into a form recognizable by EHR information system 130. For instance, EWD 201 may include call to wrapper methods 203, which transform the API call into a call method by wrapping and/or otherwise encapsulating the content (e.g., physician's input). EWD 201 may add header information to the API call or its content. The header information may be recognized and used by EHR information system 130 to obtain the physician's input (e.g., requested patient record). Additionally, EWD 201 may add trailer information to the API call or its content to signify the end of the message.

EHR information system 130 may receive and parse the call method to obtain the physician's input. Using a core method 207 (e.g., business logic rules), EHR information system 130 may use the physician's input to determine whether to update various financial and administrative services with respect to the hospital, physician, medical department, and/or patient. As an example, if the input is an order for a prescription drug, the hospital's pharmacy may be notified. The drug may be reserved for the patient and the drug's inventory may be updated. Additionally, financial services may be updated. For instance, the patient's insurance company may be notified and the patient may be billed for the drug. Additionally, financial services may be notified if the hospital's pharmacy intends to order more of the prescribed drug and how much it will cost the hospital. As noted above, EHR information system 130 may perform any services of the VistA system.

EHR information system 130 may use the physician's input and data obtained from EHR database 211 as data fields in the execution of routines 209. For instance, EHR information system 130 may, based on the user's input and a first set of routines determine, identify data (e.g., the patient's medical record, clinical data, etc.) to retrieve from EHR database 211 for use with a second set for routines (e.g., medical diagnosis rules, medical ontologies, et). Medical knowledge ontologies may represent knowledge of a set of medical concepts within a particular medical domain and the relations between those concepts.

Additionally, EHR information system 130 may write information to and retrieve information from EHR database 211 (e.g., a MUMPS database). As an example, EHR information system 130 may retrieve patient health records. As another example, EHR information system 130 may update patient health records based on physician input.

Once EHR information system 130 determines an appropriate response to the physician's input using the core method 207, routines 209 and/or EHR database 211, EHR information system 130 may output an array response with the appropriate response to EWB 201. The appropriate response may include the patient's medical health record, analysis resulting from routines 209 and/or medical knowledge ontologies (e.g., an indication that the patient may be suffering from a particular disorder, indications of recommended prescription drugs, an indication of impending medical emergencies, etc.), each of which will be explained in further detail below. Further, the response may include various codes under the Systematized Nomenclature of Medicine (snowmed).

EWB 201 may, in its role as a gateway, use an array to JSON response method 213 to format the array response into a JavaScript Object Notation (JSON) response and send the JSON response to webserver 105, which may then relay the JSON response to the app connectivity layer of mobile device 109 for use by the user-friendly medical app. Once received, the user-friendly medical app may then construct (or update) its user interface from the JSON response to display the information therein (e.g., the patient's medical record). For instance, the app may dynamically use the response's content to determine how to present (e.g., order) the information. As an example, the user-friendly medical app may generate a single user interface with all of the response's content displayed to the physician. The user interface may include multiple tiles (e.g., mini-windows) where each tile displays information having a different attribute, as will be explained in further detail below.

Architecture 200 may include other backend services 215, which may store preferences and customization information specific to each physician for use in modifying messages. For instance, backend services 215 may intercept communications (e.g., API calls, JSON responses, etc.) between mobile device 109 and EHR information system 130, and may modify and/or otherwise update such communications by appending content specific to the physician to (and/or replacing content in) such communications.

In one illustrative example, the physician may select a significant button on the user interface for a particular patient in order to view information significant to the patient and the particular physician, briefly described here and described in further detail below. Selection of the significance button may cause the user-friendly medical app to generate an API call and send to backend services 215 via webserver 105. Whether particular patient information is significant to a physician is subjective as it depends on that particular physician's role or task. For instance, while a lump in the chest is of high-significance to a physician tasked with determining whether a patient has breast cancer. The lump in the chest might not be significant to a surgeon performing an appendectomy on the same patient. Accordingly, backend services 215 may, using a physician identifier in the API call generated by mobile device 109, identify the physician and/or the physician's role or task. For instance, backend services 215 may have a pre-defined set of fields that are significant either to that physician or that physician's role. In some instances, physicians may set and/or otherwise define the fields that are significant to them. Backend services 215 may update the API call to additionally request data pertaining to those fields so that the physician may obtain data this is significant to that physician and forward the update API call to webserver 105 for relay to EHR information system 130.

In another illustrative example, backend services 215 may intercept a JSON response being relayed from EHR information system 130 to mobile device 109 via webserver 105 to account for the requesting physician's preferences and customizations. For instance, backend services 215 may identify the requesting physician based on the physician's identifier included in the JSON response and determine that physician's preferences and customizations for the user-friendly medical app. The physician's preferences and/or customizations may be defined by the physician and/or dynamically determined based on the physician's treatment history for the particular patient ailment/symptom being treated. As an example, backend services 215 may determine the patient ailment, symptom or diagnosis specified by the physician and, using such information, may identify which prescription medications that physician most frequently prescribes and appending priority information to the JSON response so that the user-friendly medical app gives deference to the frequently prescribed medications when it lists recommended prescribed medications to the physician (e.g., listing the physician's most frequently prescribed medications at the top of the list). As another example, the physician may have defined a particular user interface layout of the tiles described below. Backend service 215 may append the layout information to the JSON response and forward the updated response back to webserver 105 for relay to mobile device 109.

Figure 7:
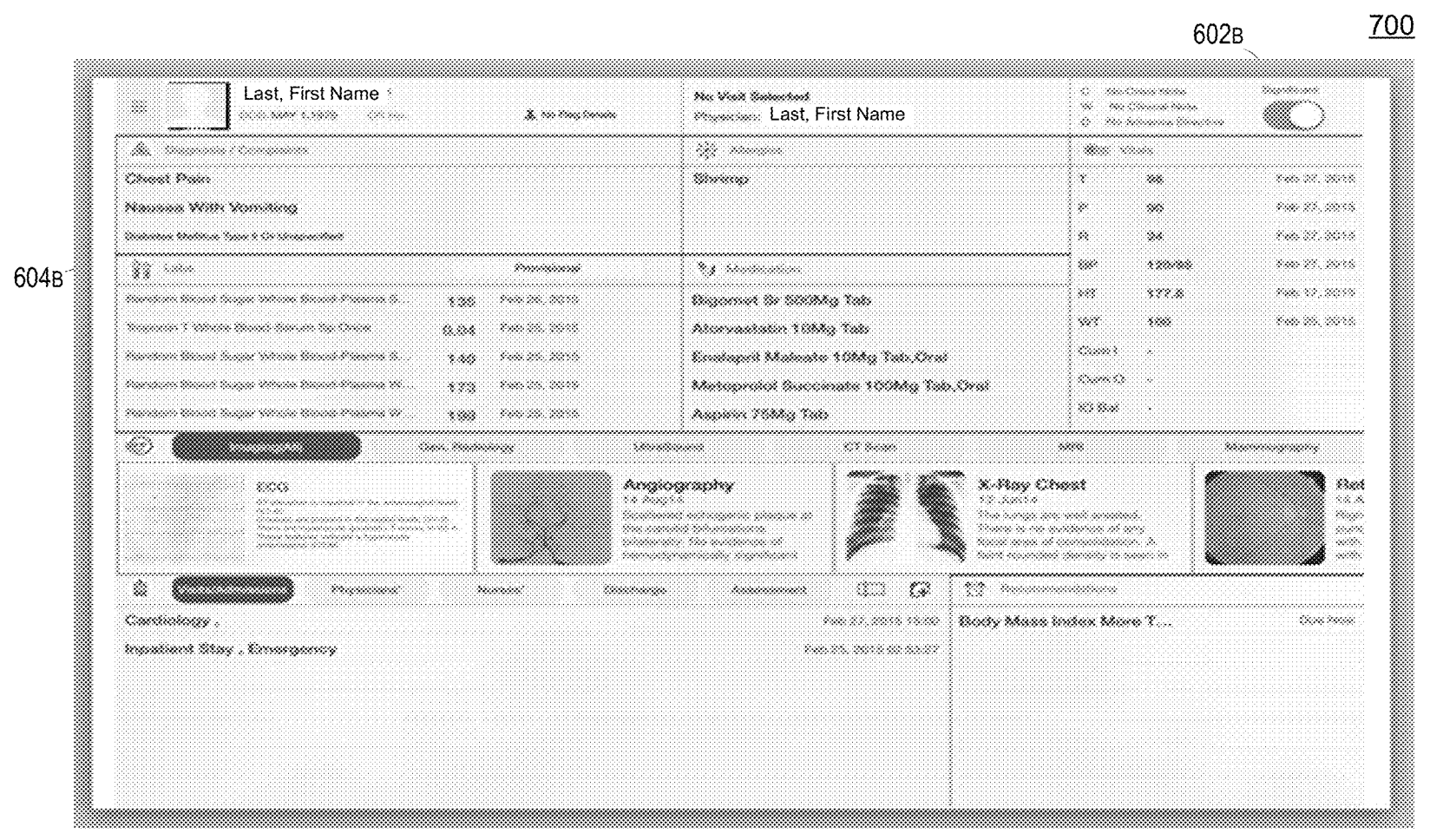

Backend services 215 may store clinical data that includes a range of acceptable values for a particular field of an EHR (e.g., acceptable levels/values of troponin T whole blood-serum sp once) for a patient. In some embodiments, acceptable ranges/values for the particular field may be specific to a demographic. As an example, acceptable values/level of a particular field for patients of one particular gender, age, and/or race may be different from those for patients of a different gender, age, and/or race. Further, backend services 215 may work in tandem with the user-friendly medical app installed on mobile device 109 to permit a physician to customize the range of acceptable levels/values for a particular field so that the range is specific to a particular patient. Backend services 215 may link and store the customized range with the patient's EHR. In one example, an acceptable range of troponin T whole blood-serum sp once may be between 0 and 1 for males and 0.5 and 1.2 for females. A physician may modify the acceptable range of troponin T whole blood-serum sp for a particular male patient's to be between 0.1 and 0.8. As a result, as shown in FIG. 7, the particular male patient's 0.04 value may be shown in red as significant to the physician since 0.04 is not within the customized range specified by the physician even though 0.04 may fall within the typical acceptable range for a male patient.

In some embodiments, functionality described above as being performed by backend services 215 may be performed locally by mobile device 109. In such embodiments, backend services 215 might not be included in architecture 200.

Figure 3:
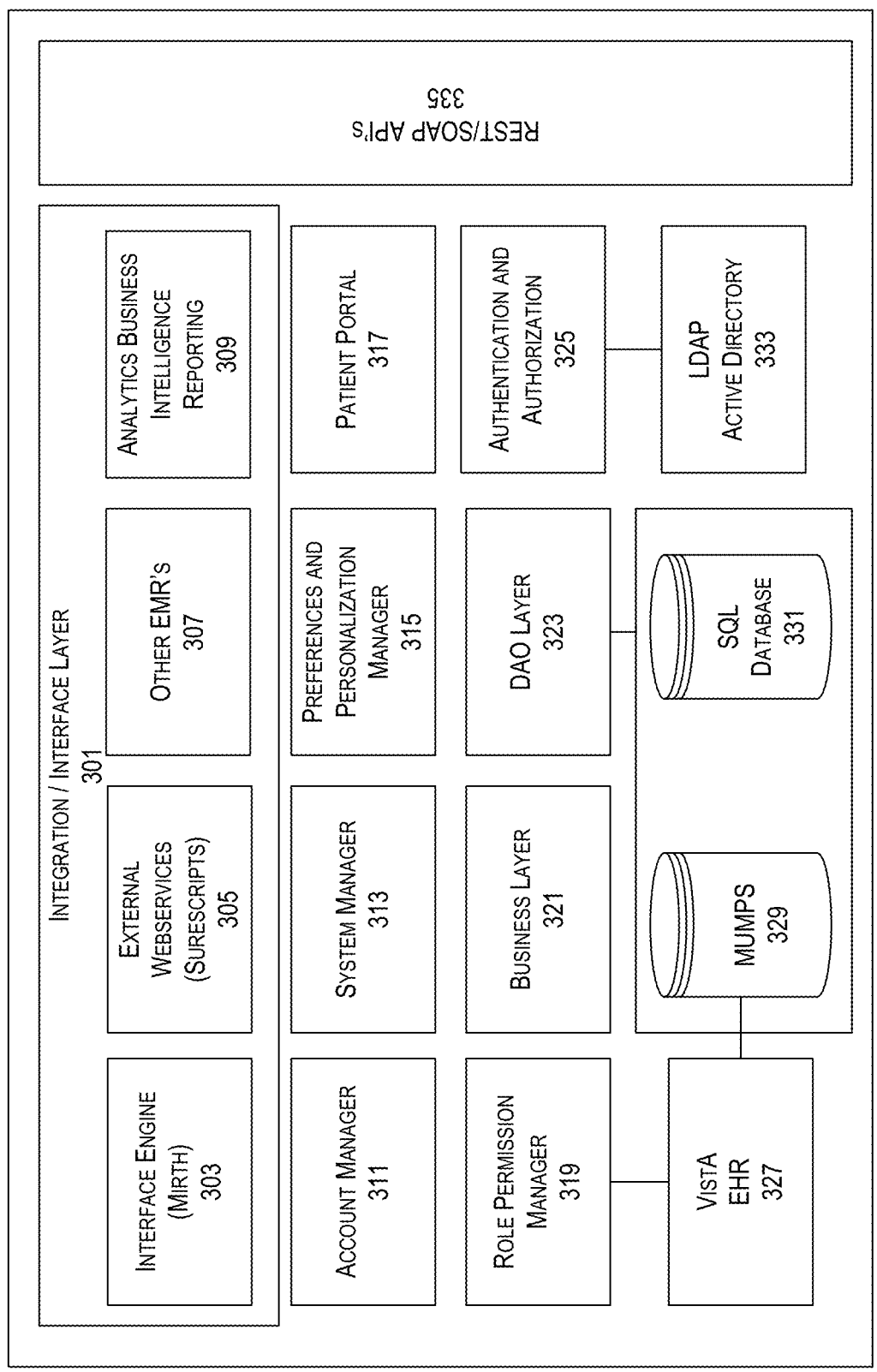
FIG. 3 depicts an illustrative view of various modules and layers of the user-friendly system in accordance with one or more aspects described herein.

FIG. 3 depicts an illustrative view of various modules and layers of the user-friendly system 300 in accordance with one or more aspects described herein. System 300 includes an integration and interface layer 301, which may include an interface engine 303 to other systems (e.g., MIRTH), an interface to external webservices 305 (e.g., surescripts), an interface to access other electronic medical records (EMRs) 307, and an interface to analytics business and intelligence reporting 309. System 300 may include multiple user-facing modules including an account manager 311 to manage accounts of various users, system manager 313, preferences and personalization manager 315, a patient portal 317 to allow patient access to their medical records via a webpage, and a role permission manager 319 to manage which medical professionals may access patient records. Preference and personalization manager 315 may manage various functions of the user-friendly medical app and/or backend services 215 including, for example, each physician's preferences and customizations, tile-interface, significant button functionality, and/or other functions.

System 300 may include other modules and layers such as a business layer 321, a data access object (DAO) layer 323, an authentication and authorization module 325, and a lightweight directory access protocol (LDAP) active directory 333. Business layer 321 may include numerous modules including, for example, laboratory module, a module for each medical department (e.g., a surgery module, a radiology module, an oncology module, etc.), policy module, procedure module, and/or other modules. DOA layer 323 enables the user-friendly medical app to communication with various modules and databases described herein. LDAP active directory 333 manages user access to the system by storing user credentials used in authentication by the authentication and authorization module 325. Directory 333 stores information on which applications a user (e.g., physician, patient,) has access to across all applications for an institution (e.g., hospital).

System 300 may also include access to an information system 327 such as VistA to access EHRs of patients and its corresponding databases (e.g., MUMPS database 329, SQL database 331). SQL database 331 may store administrative side of the patient's record, waste management information, etc. System 300 may also include representational state transfer (REST) and subjective, objective assessment plan (SOAP) application programming interfaces (APIs) 335 to interact with REST and SOAP services.

Figure 4:
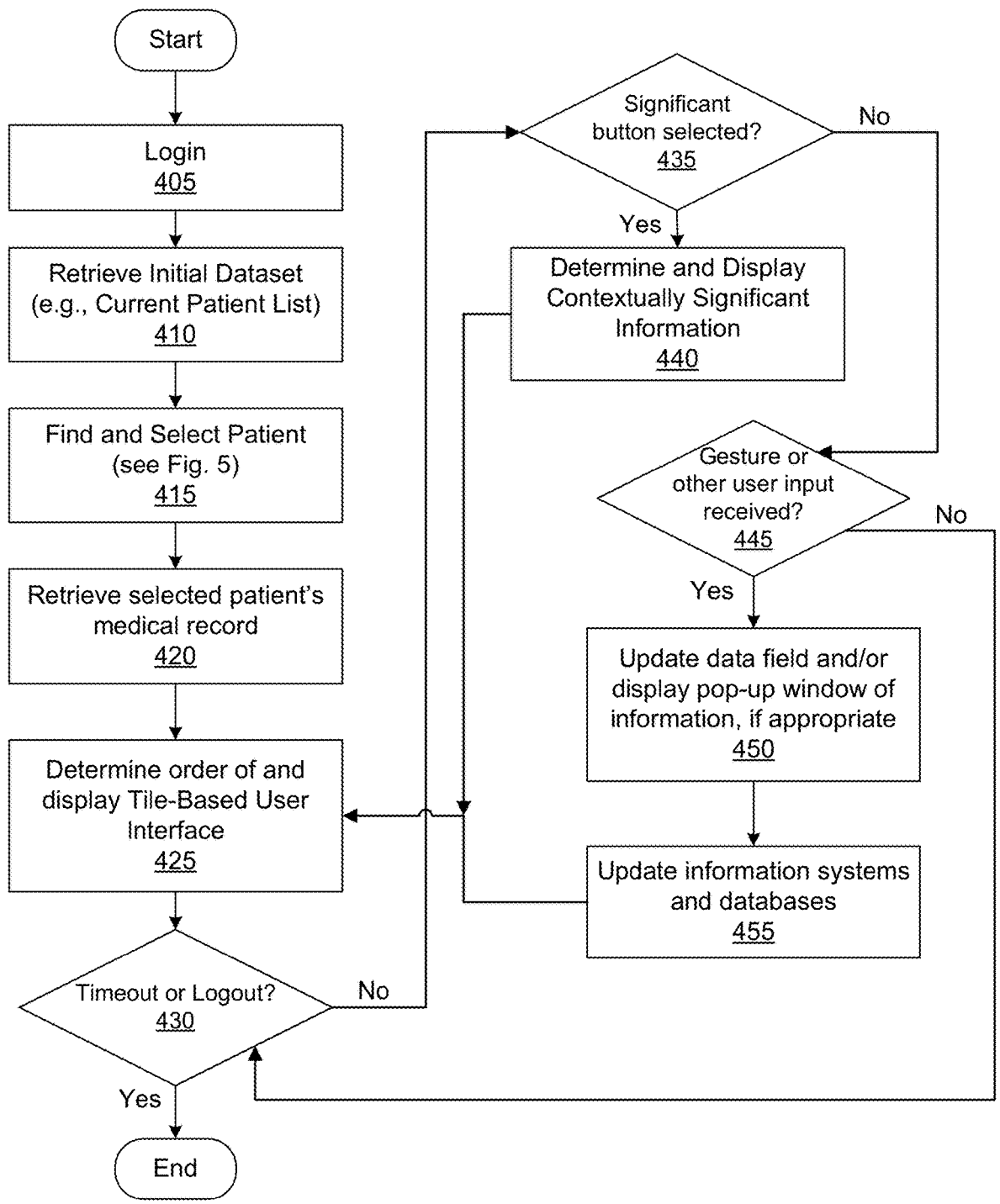
FIG. 4 depicts an illustrative flowchart for utilizing a user-friendly health management system in accordance with one or more illustrative aspects discussed herein.

FIG. 4 depicts an illustrative flowchart for utilizing a user-friendly health management system in accordance with one or more illustrative aspects discussed herein. In one or more embodiments, the method of FIG. 4 and/or one or more steps thereof may be performed by one or more computing devices. In other embodiments, the method illustrated in FIG. 4 and/or one or more steps thereof may be embodied in computer-executable instructions that are stored in a computer-readable medium, such as a non-transitory computer-readable memory. In some instances, one or more of the steps of FIG. 4 may be performed in a different order. In some instances, one or more of the steps of FIG. 4 may be omitted and/or otherwise not performed. Functionalities discussed herein as being performed by mobile device 109 may have been caused to be performed by the user-friendly medical app installed on mobile device 109.

As seen in FIG. 4, the method may begin at step 405 in which a physician may login to the user-friendly app installed on mobile device 109. For instance, the physician may enter the physician's user credential (e.g., username and password, tokens, etc.) via mobile device 109. In one or more arrangements, mobile device 109 may locally authenticate the physician using locally stored user authentication credentials. In one or more other arrangements, mobile device 109 may transmit the physician's authentication credentials to a remote server for authentication and, in response, may receive an indication of whether or not the physician is authorized to access the user-friendly medical app. If not, the user-friendly medical app may notify the physician that the physician has not been authenticated and may prompt the user to enter the physician's authentication credentials.

Otherwise, if the physician is authorized to use the user-friendly medical app, then, in step 410, mobile device 109 may retrieve an initial dataset from one or more other computing devices discussed herein (e.g., EHR information system 130, EHR DB 132, backend services 215, etc.) for use by the user-friendly medical app. The initial dataset may include any information discussed herein. As an example, the initial dataset may include a current list of patients currently receiving care at the hospital. As another example, the initial dataset may also include the electronic health records of those patients. As yet another example, the initial dataset may include customization and preference information of the physician that just logged into the user friendly medical app in step 405. As still yet another example, the initial dataset may include information for use with the significant button (e.g., data fields of significance to that particular physician). In some instances, the initial dataset may be received after the physician has logged into the user-friendly medical app. In other instances, the initial dataset may be received prior to login (e.g., the initial dataset may be sent to mobile device 109 when the device is registered with the institution), or some other time.

In step 415, mobile device 109 may display a dynamic and interactive user interface to enable the physician to find and select a patient. As shown in illustrative user interface 500 of FIG. 5, the physician has a number of options by which to find a patient. User interface 500 may include a search bar that enables the user to enter a patient identifier (e.g., name, patient number, etc.) to lookup the patient's electronic health record from e.g., EHR information system 130, EHR DB 132, etc. The physician may enter the patient identifier via a physical input device (e.g., physical keyboard), onscreen input device (e.g., an onscreen keyboard), voice input, optical input (e.g., a bar code scan), etc.

In response to entering the patient identifier, user interface 500 may dynamically update its output to display a list of patients matching the physician's input. Optionally, the list may include a summary of each patient's information (e.g., name, age, date of birth, assigned physician, hospital department location, room location, appointment date/time, notifications, diagnosis/complaints, vitals information, prescribed medications, laboratory results, and the like). In some instances, only a subset of patients may initially be displayed in the list. In such instances, the physician may gesture (e.g., scroll up, scroll down, etc.) or submit some other user input to receive the next subset of matching patients or, alternatively, the entire list of matching patients.

The physician may select (e.g., via a touch-based input on the screen of mobile device 109) a number of filters to help narrow down the search results. For example, the physician can select an "all" button to view all matching patients, a "new patient" button to view only those patients who are new (e.g., have only been patients for less than a preset time period), an "abnormal" button to view patients that have been designated as abnormal either administrative or medically, and the like. Additional filters may include searching for patient by appointment, by insurance provider, by clinic, by ward, and the like.

In response to each of the physician's inputs, mobile device 109 may determine whether there are any matching results stored in its own local memory and, if so, display those results. Additionally or if there are not any matching results stored in its own local memory, mobile device 109 may submit an API call to retrieve the results from EHR information system 130, EHR DB 132, backend services 215 in a similar manner as discussed above in FIG. 2.

In step 420, the physician may select (e.g., via an onscreen touch input) a particular patient in the listing to obtain the patient's medical record, medical knowledge, laboratory results, clinical data, administrative data, or other information discussed herein. Mobile device 109 may first determine whether such information is locally available in its local memory and retrieve any information not found in its local memory from EHR information system 130 as described above in FIG. 2.

Once the patient's electronic medical record is received by mobile device 109, mobile device 109 may, in step 425, determine a layout order in which to present the tiles. In some instances, the layout order may be selected from a group of preset layout orders. One of the preset layouts may include a default (e.g., standard) layout order. Another preset layout may have been preset by the physician or other medical professional for the particular diagnosis or treatment of the patient. Another preset layout may have been selected by the physician or a different physician for that particular patient. Another preset layout may be specified by the hospital for a particular medical department (e.g., radiology may have its own specific tile-based layout, surgery may have its own different tile-based layout, etc.).

Mobile device 109 may select the default layout when there are no better suited layouts (e.g., there is not another preset layout specific to the physician, patient, diagnosis, treatment, etc.). Otherwise, mobile device 109 may select the preset layout that for the physician, patient, diagnosis, treatment, etc. If there is more than one matching preset layout, mobile device 109 may use tie-breaking rules (e.g., received with the initial dataset). In some instances, the tie-breaking rules may be specified by the physician, hospital, or other medical entity. As a result, the tie-breaking rules of one physician may be different than the tie-breaking rules of another physician. As an example, one physician may specify that if there is a preset layout specific to the patient and a preset layout specific to the physician, then mobile device 109 should select the preset layout specific to the patient. A different physician may specify that if there is a preset layout specific to the patient and a preset layout specific to the physician, then mobile device 109 should select the preset layout specific to the physician.

A tile-based layout may include multiple different tiles. Each tile may be specific to a particular attribute or category of information (e.g., diagnosis, allergies, laboratory results, medications, recommendations, etc.), and include one or more preset fields to be populated using the patient's electronic medical record, medical knowledge, laboratory results, clinical data, administrative data, or other information discussed herein. Each of the fields within a particular layout may be customized the physician, department, or institution who defined the particular preset layout. As a result, different tiles that are directed the same category may include different fields for different physicians. As an example, one physician may include fields for all laboratory test results of the patient whereas another physician may only include fields for a subset of all of the laboratory test results of the patient.

The tile-based interface may be streamlined into single screen of tiles. There may also be tiles for information, documentation, treatment plan implementation, and prescription. Using the tile-based interface, a physician may view a patient's medical records, enter a treatment plan and document all using a single user interface in a non-linear (e.g., non-sequential) order, as will be discussed in further detail below. Each tile can perform a number of functions. For instance, a tile may display information concerning the patient entered in sessions by the physician or other medical professionals.

Figure 6:
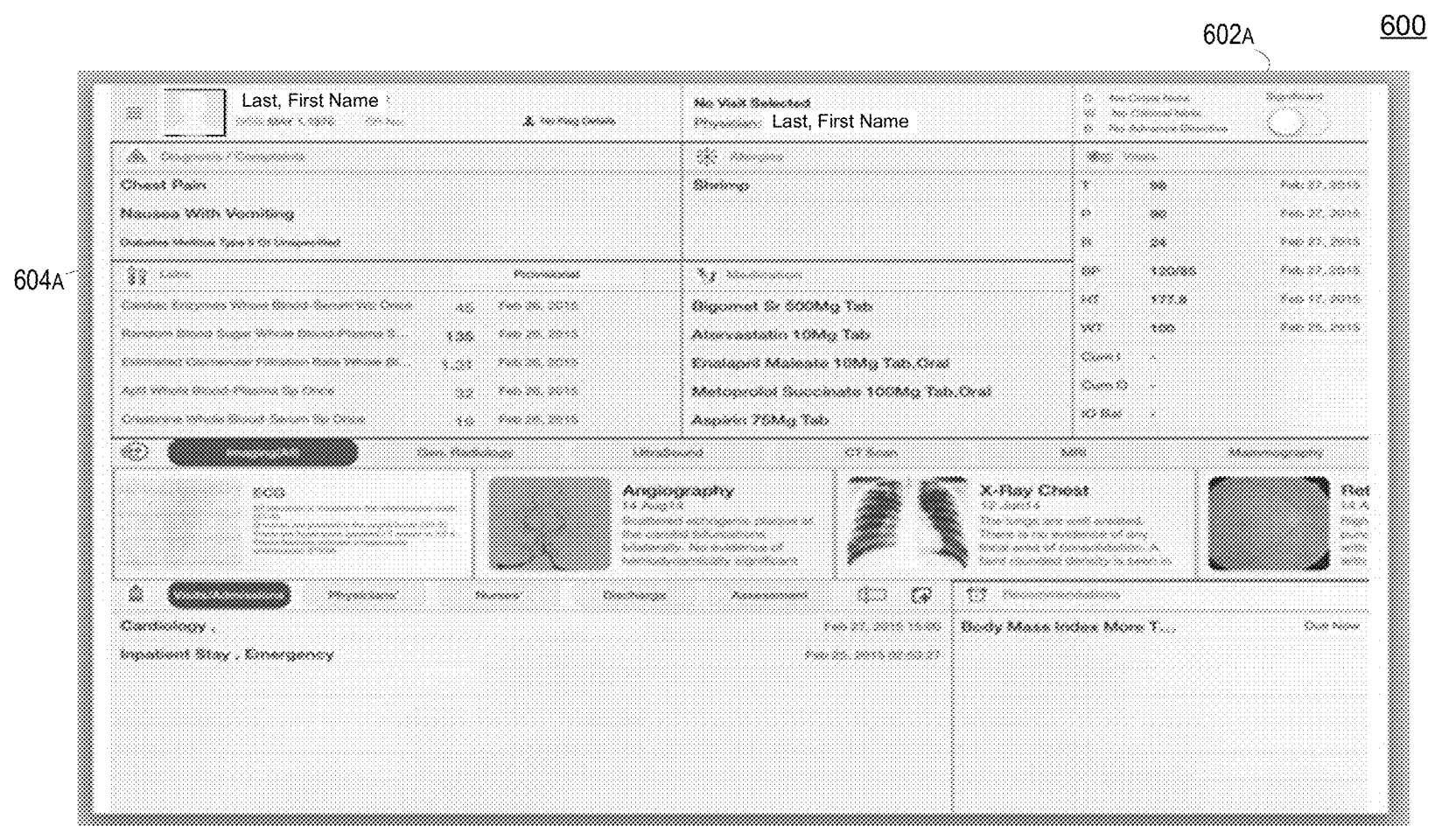

Once the fields are populated with values from the patient's electronic medical record, medical knowledge, laboratory results, clinical data, administrative data, or other information discussed herein, mobile device 109 may display the patient's electronic health record and other information relevant to the physician in a tile-based user interface 600 as shown in FIG. 6. In this example, the layout includes a general patient information tile that includes the patient's name, date of birth, room location, etc. The layout also includes a tile for diagnosis and complaints of the patient, a tile for the patient's allergies, a tile for the patient's vitals, a tile for the patient's laboratory test results, a tile for the patient's medications, a tile for imaging (e.g., radiology images, ultrasound images, CT scan images, MRI images, mammography images, etc.), a tile for visits and admissions, a tile for attending physicians and nurses, a tile for discharge, at tile for assessment, a tile for recommendations by either a physician or by the user-friendly app using based on an analysis of the patient's medical information in relation to medical knowledge (e.g., ontologies, clinical data, etc.). Each of the tiles may be resized (e.g., made larger or smaller, collapsed, expanded), scrollable to view additional information, etc.

In step 430, mobile device 109 may determine whether the physician has logged out or been inactive for at a preset time period to constitute a timeout. For instance, the physician may select a logout button or close the user-friendly medical app to logout of the app. The physician may be considered inactive when the physician is not interacting with mobile device 109 or the user-friendly medical app. For instance, mobile device 109 may start a counter when the physician interacts with mobile device 109 (or, alternatively, the user-friendly medical app) and may reset the counter to zero when the physician subsequently interacts with mobile device 109 (or, alternatively, the user-friendly medical app). If the counter exceeds a preset timeout threshold, mobile device 109 may logout the physician from the user-friendly medical app and end the physician's session with EHR information system 130.

Figure 5:
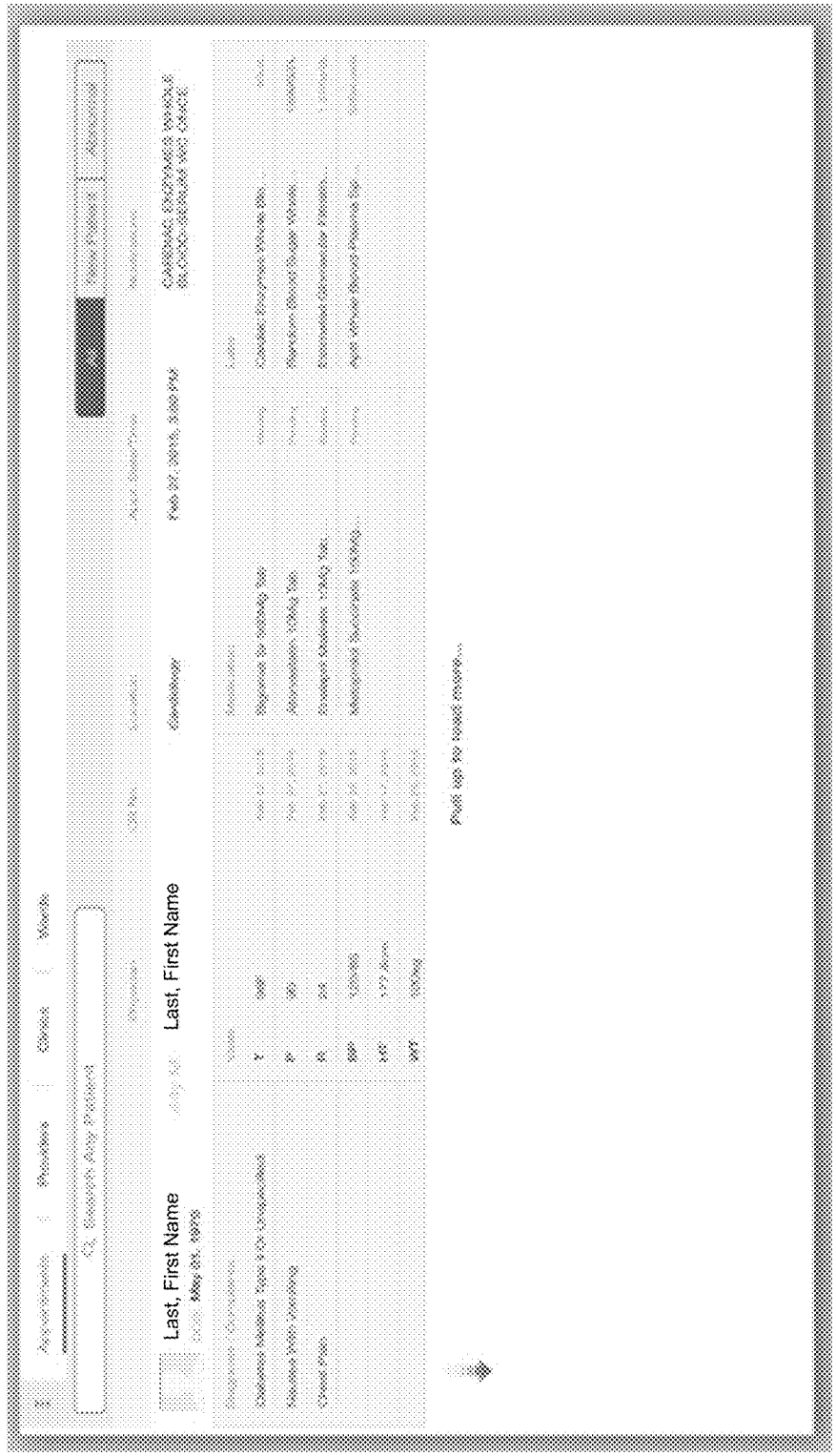
FIG. 5 depicts an illustrative view of a user interface for searching for a patient in accordance with one or more illustrative aspects discussed herein.

In step 435, if mobile device 109 receives user input from the physician (e.g., an onscreen touch) prior to the timeout threshold being reached, mobile device 109 may determine if the physician selected the significant information icon button 602, which is shown in FIG. 5 in an unselected state 602a and in FIG. 7 in a selected state 602b. If mobile device 109 determines that the significant button 602 has been selected by the physician, mobile device 109 may, in step 440, determine what information is significant to that physician for that particular patient using one or more significance policies and display the significant data values. Mobile device 109 may, in step 420, receive significance information for the particular patient. The significance information is also specific to the particular physician. As an example and as discussed above, a physician tasked with finding breast cancer may find that a lump in the chest is significant information while a surgeon performing an appendectomy on the same patient might not find the lump in the chest significant. Custom data ranges for various data fields in the tiles may be specified as significant if the patient's data value for that field lies outside of (or, alternatively, falls within) the custom data range. The data range may be set by the physician, a medical department, the medical institution, and/or the medical industry (e.g., an industry standard). The custom range may be adjusted for the particular patient by the physician or other medical professional (e.g., another physician) so that the range is specific to that patient since the physician is treating the patient and is aware of other circumstances that may affect the range of acceptable or unacceptable values. Further, if the custom range is adjusted to be specific to the patient, backend services 215 may identify the physician that adjusted the range and permit storage of notes input by that physician as to the reasons or justifications the range was adjusted for this patient.

In one or more arrangements, mobile device 109 may determine whether a data value from the patient's electronic medical record for a particular data field is within an acceptable range of data values specified in the significance information. If so, the data value may be identified as insignificant (e.g., normal) since it is within acceptable limits. Optionally, the data value might not be displayed when the significance button 602 is in its active state 602b. In some instances, only a subset of the normal data values may be filtered out (e.g., not displayed while other normal data values are displayed). Otherwise, if the data value is not within an acceptable range of data values specified in the significance information, mobile device 109 may identify the data value as significant (e.g., abnormal) and may determine if the abnormal value is relevant to the physician based on the physician's role or task and, if relevant, may display the data value in significance-active user interface 700 as shown in FIG. 7. In some instances, the significant data value may be marked in a particular color (e.g., red), highlighted, bolded and/or otherwise indicated as being significant. Further, in some instances, data fields only slightly outside the accept range may be in one color (e.g., a data value within a preset amount from the acceptable range may be shown in a yellow color) while data fields that are more abnormal may be in a different color (e.g., a different data value that is outside the preset amount from the acceptable range may be shown in red color). In one illustrative example, the patient's laboratory results 604a as shown in FIG. 6 may be updated to include only significant lab results 604b as shown in FIG. 7. In some instances, in step 425, the tile layout may be reordered to a different preset tile layout upon activation of the significant button 502.

In one or more additional or alternative arrangements, mobile device 109 may receive indications of which data values are significant rather than locally determining whether a data value is significant. In such one or more additional or alternative arrangements, backend services 215 may determine whether data values of the patient is significant by intercepting the JSON response that includes at least the patient's electronic medical record and may also include clinical data, medical knowledge, etc. Backend services 215 may use the one or more significance polices stored in backend service 215 to determine which of the patient's data values are significant to the requesting physician in a similar manner as discussed above. Backend services 215 may tag each significant data value as being significant. As a result, in step 420, when mobile device 109 receives the patient's electronic medical record among other things, mobile device 109 may also receive indications of which data values have been tagged as significant so that mobile device 109 may later identify the data value as being significant when the significant button 602 has been activated. As an example, imaging results, procedure notes, clinical notes, recommendations, diagnosis, complaints, allergies, etc. may be tagged as significant. In some instances, a physician or other medical professional can tag data value using a preset gesture-based motion the screen (e.g., by swiping up on the data value or data item). The physician may deactivate the significant button to return to user interface 600.

Referring back to step 435, if physician did not select significant button 602, then, in step 445, mobile device 109 may determine whether a gesture or another user input has been received. If not, then the process may return to step 430. Otherwise, if a gestures or other input has been received, mobile device 109 may, in step 450, update a particular data field, display a popup window of detailed information, and/or perform another action, if appropriate. For instance, mobile device 109 may determine that the physician is attempting to update a data field and, if the field is user-editable, may permit the physician to edit that field and store the updated data value. As an example, a user may tap (e.g., perform an onscreen touch of) a tile's header to open a window to enter information in a structured format.

As another example, the user may perform an onscreen touch-based gesture (also referred to herein as a gesture) on an item displayed by mobile device 109. A gesture may be performed by the physician by touching the touchscreen of mobile device 109 and performing a predefined motion. An example of a gesture includes a swipe-based gesture where the user touches a displayed item with a preset number of fingers and moves their fingers in a particular direction on the touchscreen of mobile device 109. For instance, the user may swipe left, right, up, or down on the screen with a particular number of fingers (e.g., two, three, four, etc.) to perform different functions for the displayed item on which the gesture was performed. In some instances, a gesture may also include a temporal policy that may also be met to satisfy the gesture. An example of a temporal-based gesture is a long-hold gesture where the user touches a displayed item for at least a continuous minimum time period before breaking contact. Another example of a gesture includes a pinching gesture where the user touches two points on the touchscreen of mobile device 109 and either moves them closer together or farther apart from one another. The above list of gestures is described merely out of convenience and numerous other gestures may be used to perform functions or actions described herein.

Each gesture may be associated with a different action. For instance, swipe-left gesture with two fingers may perform a copy action and a swipe-left gesture with three fingers may perform a view detailed information action (e.g., a detailed view of tile information). Additionally, a gesture may consistently perform the same action but the results may differ based on which displayed item the gesture was performed (e.g., the action is performed in relation to the displayed item or tile). For instance, a swipe-left gesture with two fingers performed on an allergies tile may copy the patient's information while a swipe-left gesture with two fingers performed on the medications tile may copy the patient's medications.

Actions performed in response to a particular gesture being performed on a displayed icon may include performing a transaction in the computerized physician order entry (CPOE) system, displaying a pop-up window for a physician to view detailed information about the displayed item on which the gesture was performed, and displaying an actionable pop-up window for a physician to enter a note regarding the displayed item (e.g., tile) on which the gesture was performed. Actions may also include, in response to performing a gesture on a displayed icon, using information associated with the displayed item (e.g., tile) to export the information to another application, generating a report of the information, editing an existing report including the information, copying text, editing text, adding orders, copying orders, editing orders, adding complaints, editing complaints, adding comments to complaints, editing comments to complaints, adding a diagnosis, editing a diagnosis, adding a treatment plan, editing a treatment plan, adding a medication (e.g., name, amount, and frequency to be taken by patient), editing a medication, adding allergies, editing allergies, adding vitals, editing vitals, etc. An action may also include displaying options related to the displayed item on which the gesture was performed.

Using gestures are advantageous to the physician's user experience as gestures are less obtrusive, complicated, and have a lower cognitive load than point-and-click user interfaces. Through the use of gestures and the tile-based user interface, the physician may from one screen perform an action (e.g., view, edit, or copy information) based on the context of the item on which the gesture is performed. For instance, a copy gesture performed on a tile may copy the information displayed in the tile and/or information associated with the tile (e.g., view detailed information not displayed in the tile). Further, by using the gestures on a single tile-based user interface where information is easy to find and manipulate, the physician may focus on the experience and the content rather than wasting time focusing on the interaction. Further, by using the significant button, the physician may easily find information relevant to the physician. While a gesture may act as a shortcut to perform an action, there may be many other ways to perform an action. As an example, the user may right click on the displayed item or tile to perform a copy action even though there may also be a gesture for performing the same copy action.

In some embodiments, mobile device 109 may determine whether it has the information responsive to the physician's input (e.g., whether it has all of the information for a detailed view for a particular tile). If not, mobile device 109 may request the missing information from one or more of backend services 215 and/or EHR information system 130. Once the missing information is received, mobile device 109 may display the information responsive to the physician's input.

For a gesture that enables adding or editing of information when the gesture is performed on the displayed item or tile, mobile device 109 may receive user input to add or edit information associated with the displayed item or tile via a microphone, an onscreen alpha-numeric keyboard, and/or a physical alpha-numeric keyboard, etc. When information in the tile-based UI is added and/or otherwise edited, the transaction or information entered by the physician may be documented either by inserted into (e.g., appended to) or replace previous transactions or information associated with the displayed item or tile, respectively. In some instances, mobile device 109 may store deleted (e.g., removed) information in a recovery log for a preset time period (e.g., 30 minutes, 1 hour, 2 days, etc.) and/or until a preset event occurs (e.g., the updated information is synced with a remote server such as backend services 215). If the physician either unintentionally, mistakenly, or inappropriately deletes or removes patient information, mobile device 109 may recover such information from the recovery log. Once the physician enters information, the physician may perform a gesture on the entered information to add a clinical note.

Further, mobile device 109 may monitor and store metadata related to the physician's use of mobile device 109 such as the physician's inputs or other actions. For instance, mobile device 109 may monitor when and for how long a physician viewed the tile-based interface, a pop-up window, or any other displayed information using one or more timestamps (e.g., an open window timestamp, a close window timestamp). Additionally, mobile device 109 may monitor when the physician added information or edited information also using timestamps. A timestamp may include a number of fields include date (e.g., year, month, and day) and time (e.g., hours, minutes, seconds, am or pm, time zone, etc.). Timestamps may be used by mobile device 109 and/or backend services 215 to determine whether the physician is following a patient standard of care.

In step 455, mobile device 109 may update (e.g., sync the information with) EHR information system 130, backend services 215, and/or other databases (which may be collectively referred to backend services) with the information generated or edited by the physician so the backend service may update the patient's EHR and/or physician information (e.g., physician preference history, etc.). For instance, mobile device 109 may transmit the information resulting from the physician's action. As an example, if the physician added a transaction or diagnosis, mobile device 109 may transmit the added transaction or diagnosis to backend services. As another example, if the physician edited the amount a medication should be taken by the patient (e.g., lower or increased the dosage), mobile device 109 may send the updated dosage amount to the backend services. Additionally, the metadata monitored by mobile device 109 may also be sent to the backend services, which may be used to evaluate the physician or for some other purpose.

At step 425, mobile device 109 may determine, based on the physician's inputs (e.g., selection of the significant button, gestures, added information to a particular tile, editing information of a particular tile, metadata, etc.), a new order of the tile layout. The order of the tile layout may be based on or more ordering policies stored in mobile device 109 (e.g., physician frequency of use, physician-specific specified preferences, etc.). If the new order of the tile layout is different from the current layout order, mobile device 109 may dynamically reorder the tile layout (e.g., change the current tile order layout to the new tile order layout). Additionally or alternatively, in some instances, backend services 215 may determine the new tile order layout and send one or more instructions indicative of the new tile order layout to mobile device 109 for implementation.

Additionally, backend service 215 may generate one or more recommendations based on the physician's inputs for one or more tiles, the physician's preferences and/or industry specified or physician-customized clinical data. As discussed above, backend services 215 may store clinical data that may include a range of acceptable values for a particular field of an EHR (e.g., acceptable levels/values of troponin T whole blood-serum sp once) for a patient, which may be specific to a demographic and/or customized to a particular patient by a physician. Backend services 215 may use the range of acceptable values that has been customized specific to the patient in its determination of appropriate recommendations for the patient. Backend services 215 may transmit the recommendation to mobile device 109 for display. In some instances, the recommendations may be displayed in a separate tile. Additionally or alternatively, in some instances, the recommendations may be displayed in the tile to which they relate or pertain. Steps 430-455 may then be repeated.

Figure 8:
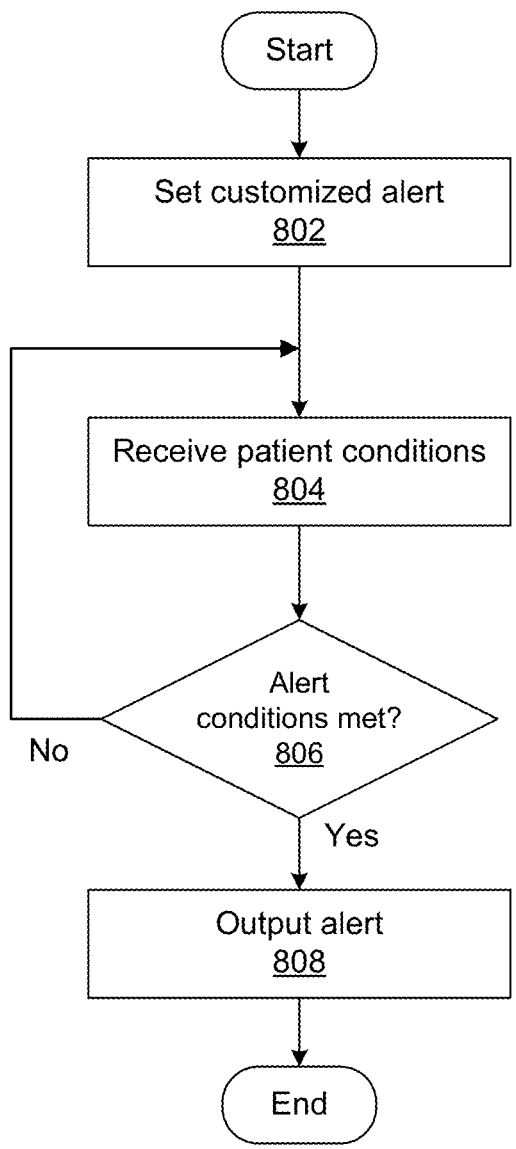
FIG. 8 depicts an illustrative flowchart for utilizing physician-customized alerts in accordance with one or more illustrative aspects discussed herein.

FIG. 8 depicts an illustrative flowchart for utilizing physician-customized alerts in accordance with one or more illustrative aspects discussed herein. In one or more embodiments, the method of FIG. 8 and/or one or more steps thereof may be performed by one or more computing devices. In other embodiments, the method illustrated in FIG. 8 and/or one or more steps thereof may be embodied in computer-executable instructions that are stored in a computer-readable medium, such as a non-transitory computer-readable memory. In some instances, one or more of the steps of FIG. 8 may be performed in a different order. In some instances, one or more of the steps of FIG. 8 may be omitted and/or otherwise not performed. Functionalities discussed herein as being performed by mobile device 109 may have been caused to be performed by the user-friendly medical app installed on mobile device 109.

As seen in FIG. 8, the method may begin at step 802 in which one or more computing devices (e.g., mobile device 109) may permit a physician to set an alert customized to the patient using the user-friendly medical app. For instance, the physician may specify one or more conditions which when met should trigger an alert. The conditions may be bodily readings of the patient (e.g., vitals, etc.). The combination of conditions set by the physician may indicative of a predicted or probable diagnosis that could occur for the patient even if the diagnosis has not yet occurred. As an example, given the patient current conditions a physician may determine that if a set of conditions occur, then the patient is likely to get pneumonia and may set an alert based on those conditions so that the physician may treat those conditions prior to the patient acquiring pneumonia. The physician may also specify who should receive the alert (which physicians, nurses, etc.), by what means (e.g., text message, email, audible sounds, etc.). The physician may also specify contents of the alert message, which may include the name or patient ID of the patient, their location in the hospital, the predicted diagnosis, the list of conditions satisfied, and/or preventative measures to be taken.

At step 804, mobile device 109 may receive the patient's conditions from one or more sources. One source may by user input into the user-friendly medical app by a medical professional (e.g., a physician, nurse, etc.). Another source may be biological measurements by machines monitoring the patient. Such machines may continuously or periodically send the patient's biological measurements to mobile device 109 (e.g., via a network). At step 806, mobile device 109 may determine whether the one or more conditions are satisfied and if so, at step 808, may output and/or otherwise transmit the alert message to the persons specified by the physician in step 802. In some embodiments, mobile device 109 may transmit the alert information (e.g., specified conditions, predicted diagnosis, etc.) to backend services 215 for storage and/or to send to other mobile devices.

Figure 9:
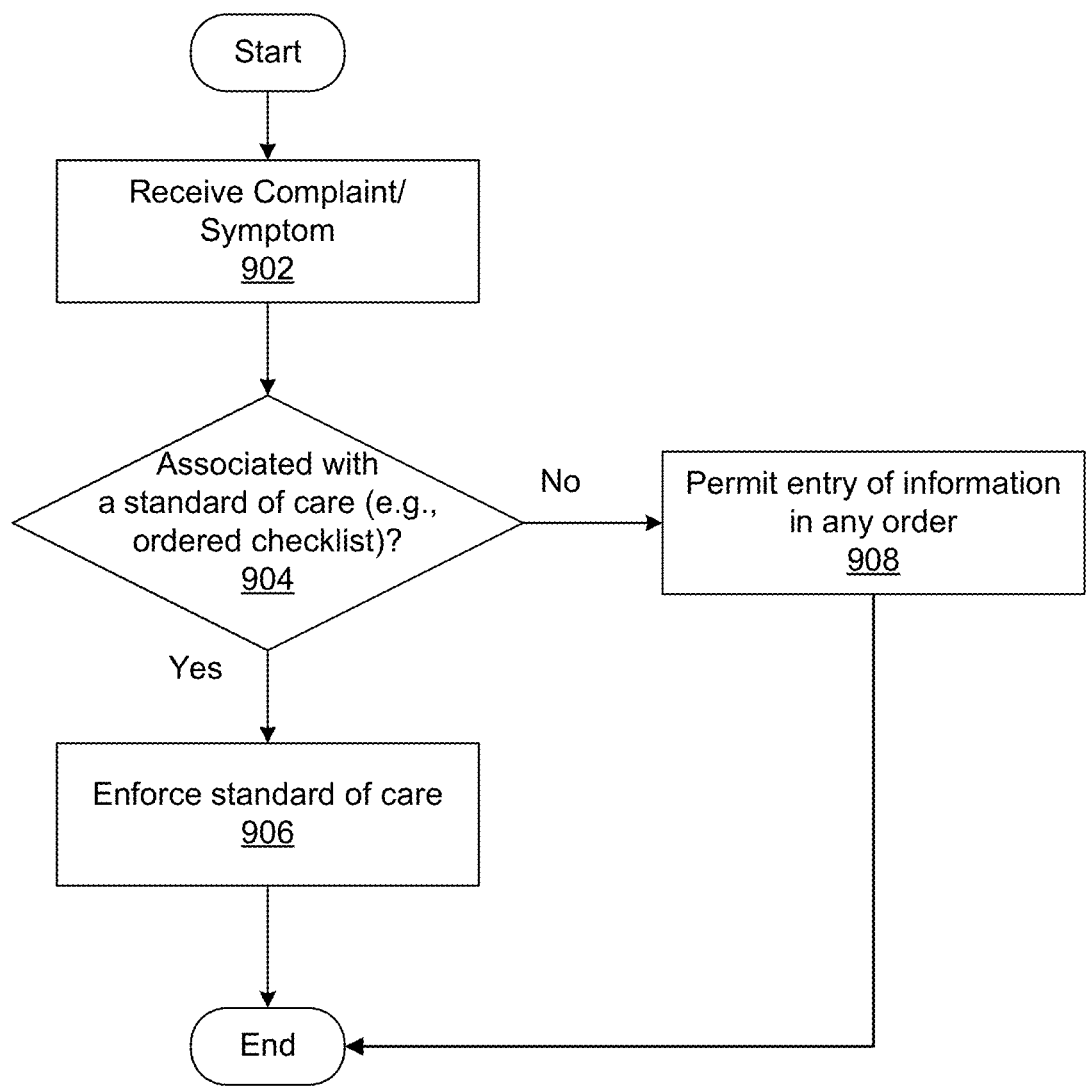
FIG. 9 depicts an illustrative flowchart for enforcing a patient standard of care in accordance with one or more illustrative aspects discussed herein.
Figure 10:
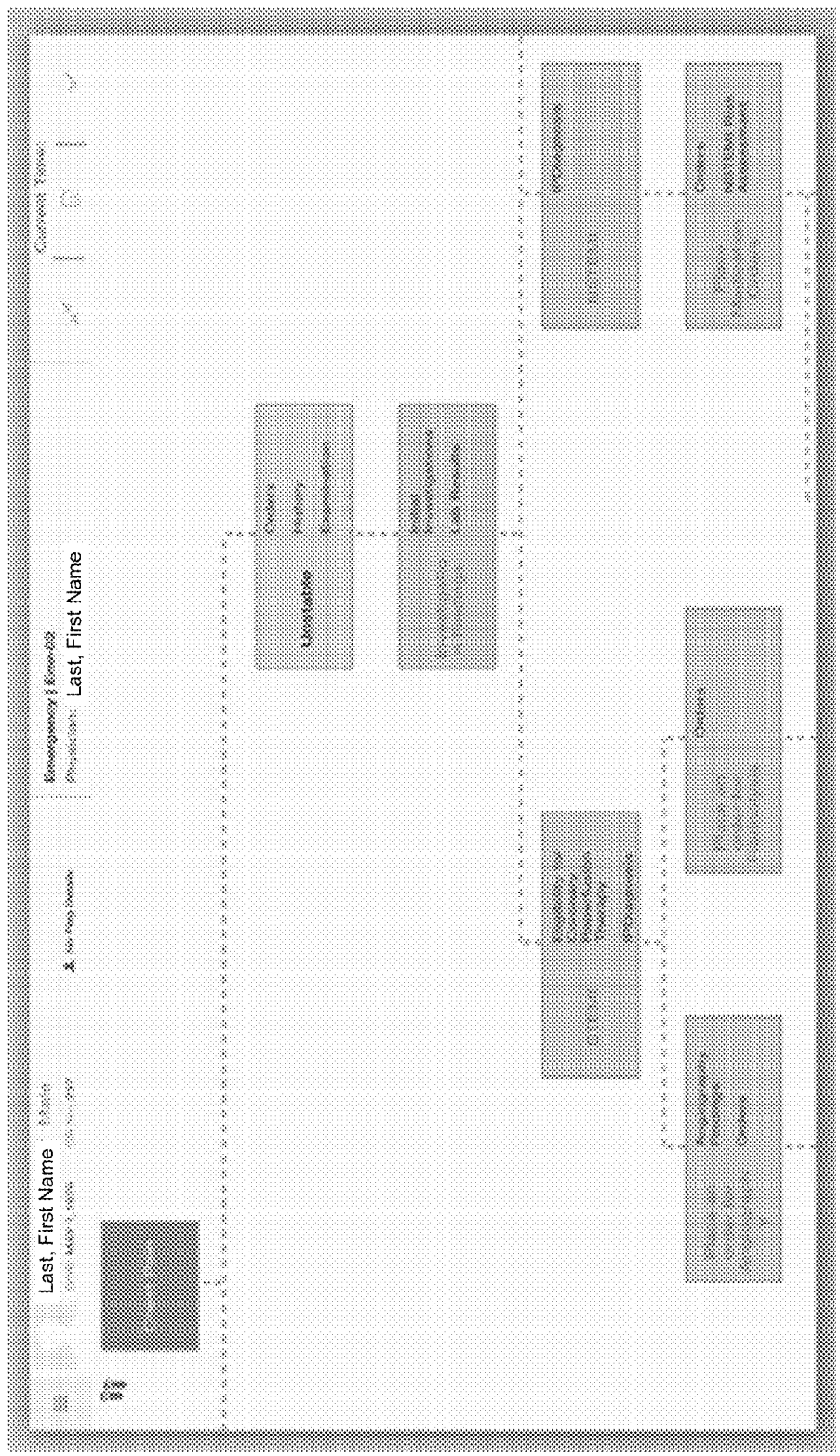
FIGS. 10-17 depict various illustrative views of a user interface for entering information according to a patient standard of care in accordance with one or more illustrative aspects discussed herein.
Figure 11:
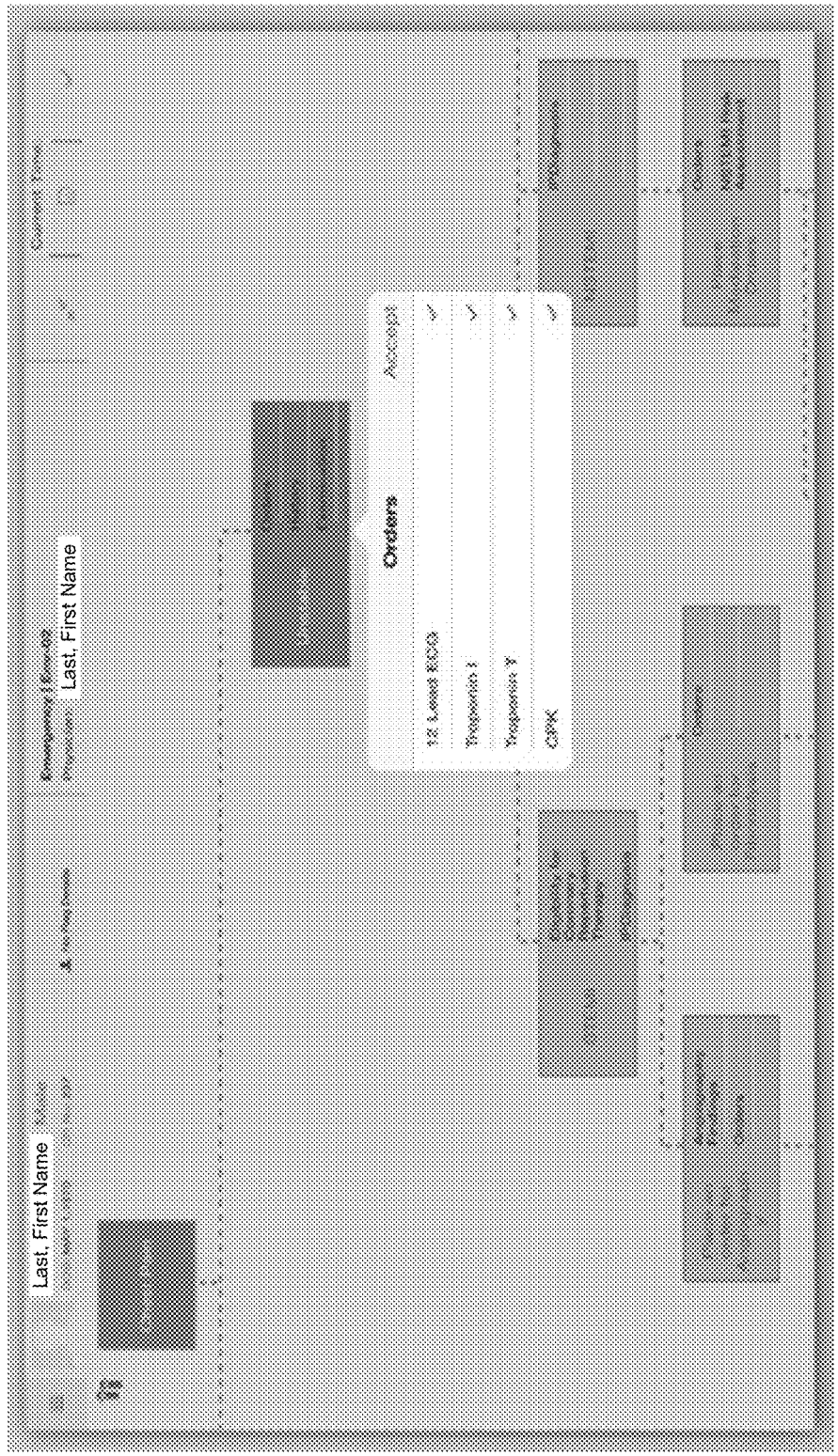

FIG. 9 depicts an illustrative flowchart for enforcing a patient standard of care in accordance with one or more illustrative aspects discussed herein. In one or more embodiments, the method of FIG. 9 and/or one or more steps thereof may be performed by one or more computing devices. In other embodiments, the method illustrated in FIG. 9 and/or one or more steps thereof may be embodied in computer-executable instructions that are stored in a computer-readable medium, such as a non-transitory computer-readable memory. In some instances, one or more of the steps of FIG. 9 may be performed in a different order. In some instances, one or more of the steps of FIG. 9 may be omitted and/or otherwise not performed. Functionalities discussed herein as being performed by mobile device 109 may have been caused to be performed by the user-friendly medical app installed on mobile device 109.

As seen in FIG. 9, the method may begin at step 902 in which one or more computing devices (e.g., mobile device 109) may receive input from a physician indicating that a patient has one or more complaints or symptoms. In some instances, the physician may select the complaint or symptom from a list (e.g., a drop down list, a dynamic auto-complete list based on received letters). The user-friendly medical app may be preconfigured with the list or may receive the list (and updates thereto) from backend services 215.

At step 904, mobile device 109 may determine whether one or more of the received complaints or symptoms are associated with a patient standard of care. A patient standard of care may be a preset ordered checklist or tree of tasks to be performed by the physician. The patient standard of care may be set by the medical industry, a particular medical institution (e.g., a hospital), a medical board, etc. The patient standard of care may be stored at backend services 215. In some instances, the patient standard of care may be sent to mobile device 109 in an initial dataset (see step 410). In other instances, once the physician selects the complaints and/or symptoms, mobile device 109 may send a request for any patient standard of cares associated with the selected complaints and/or symptoms.

Figure 12:
Figure 13:
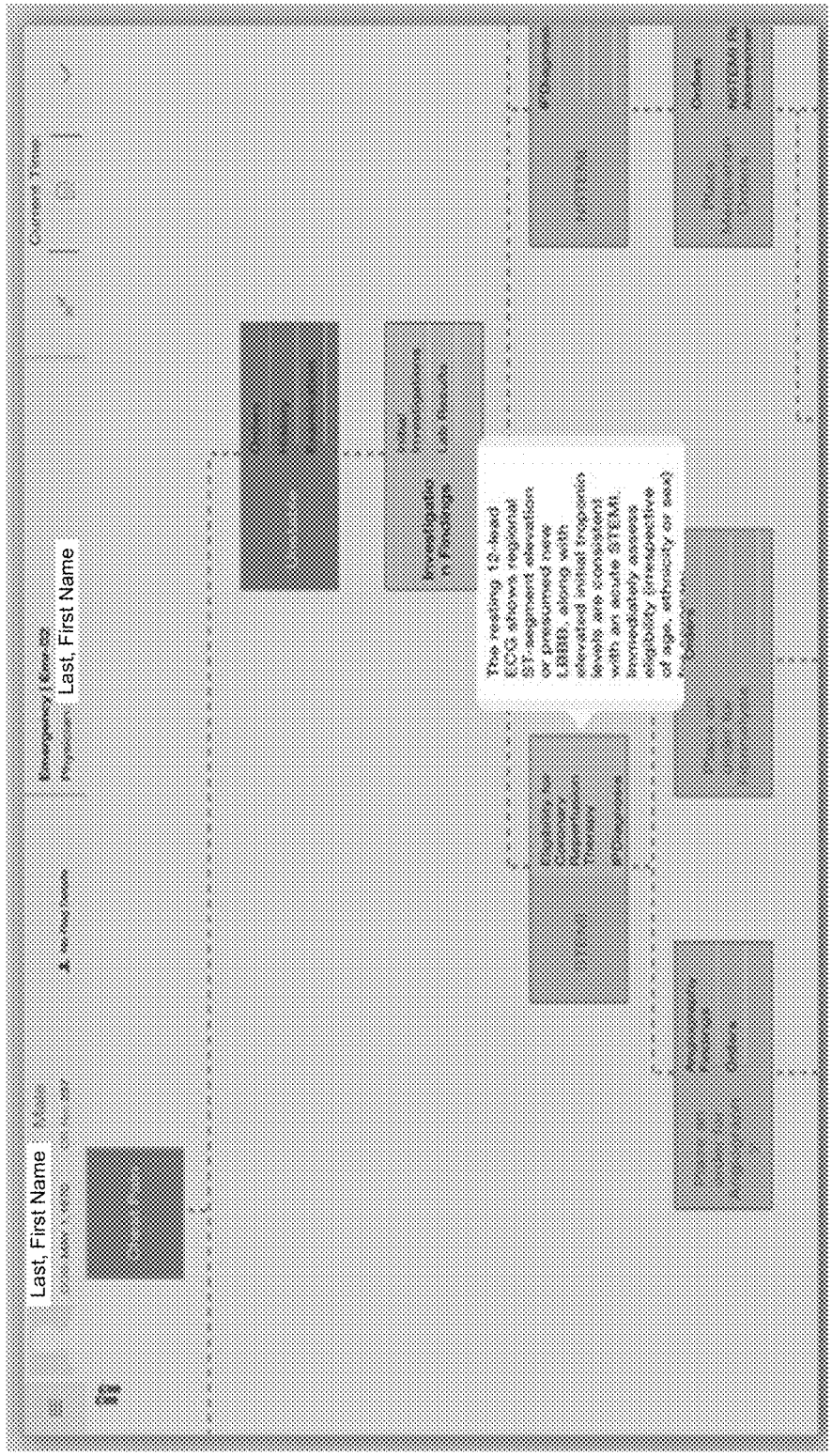
Figure 14:
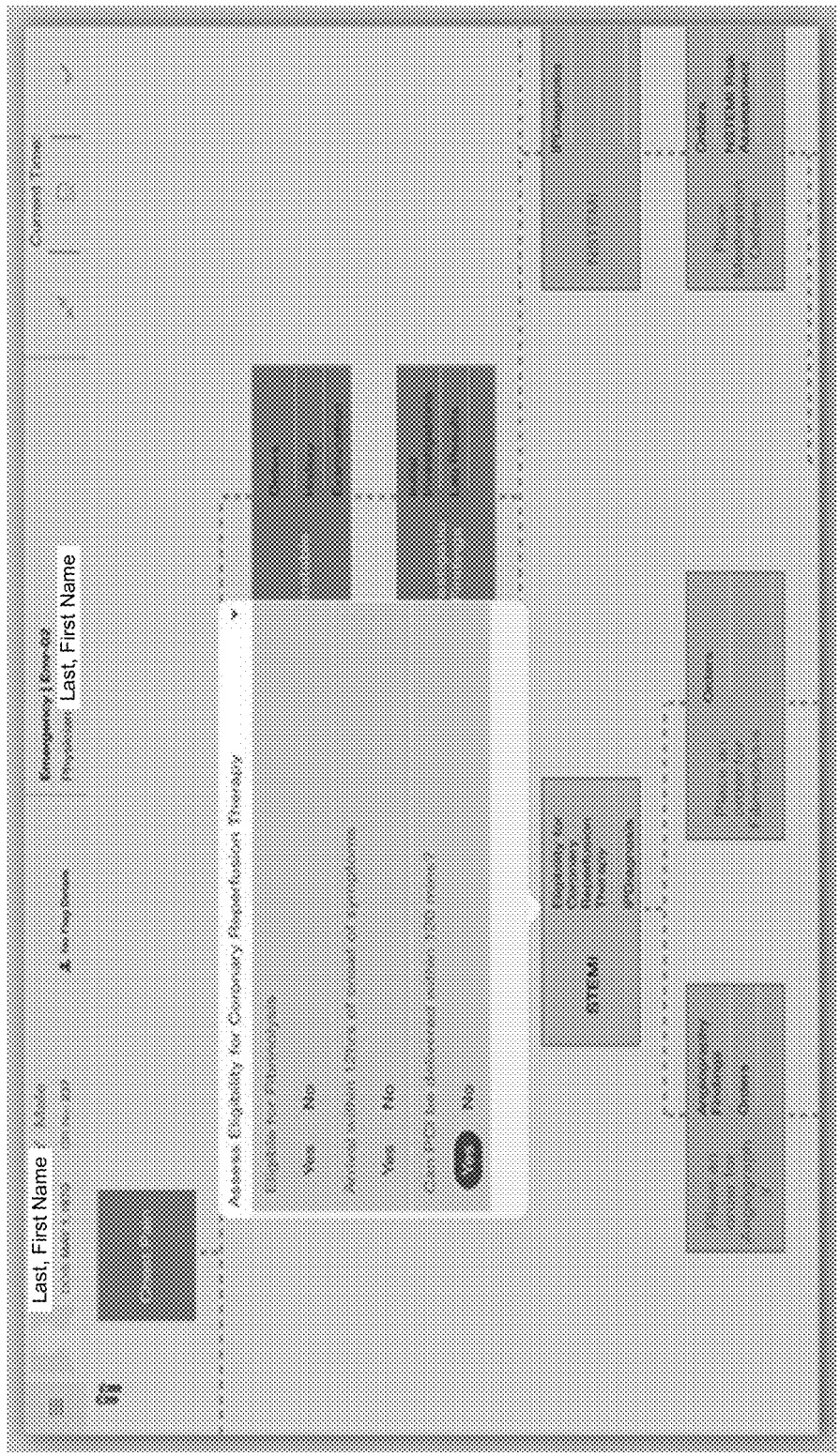
Figure 15:
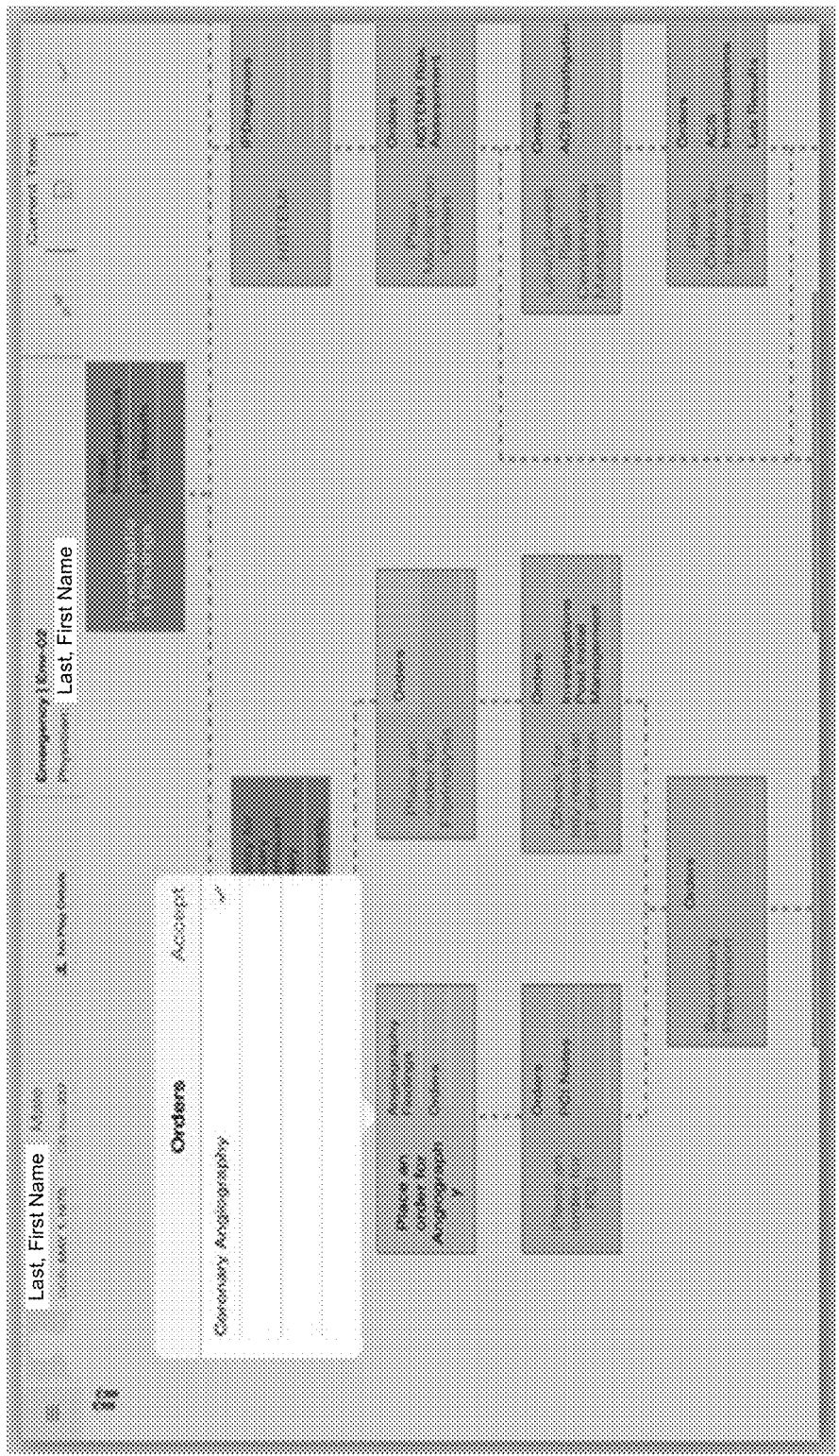
Figure 16:
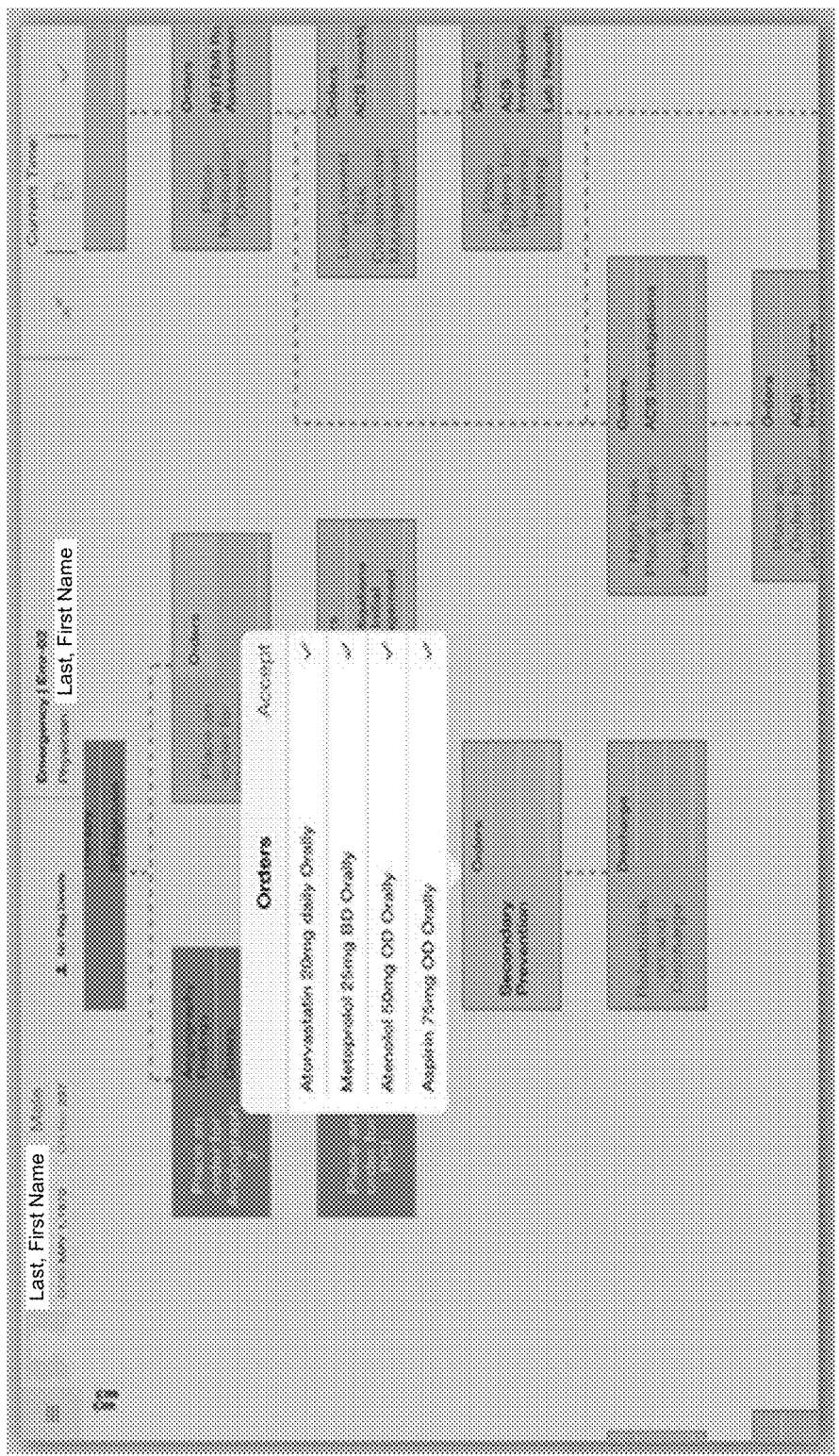
Figure 17:
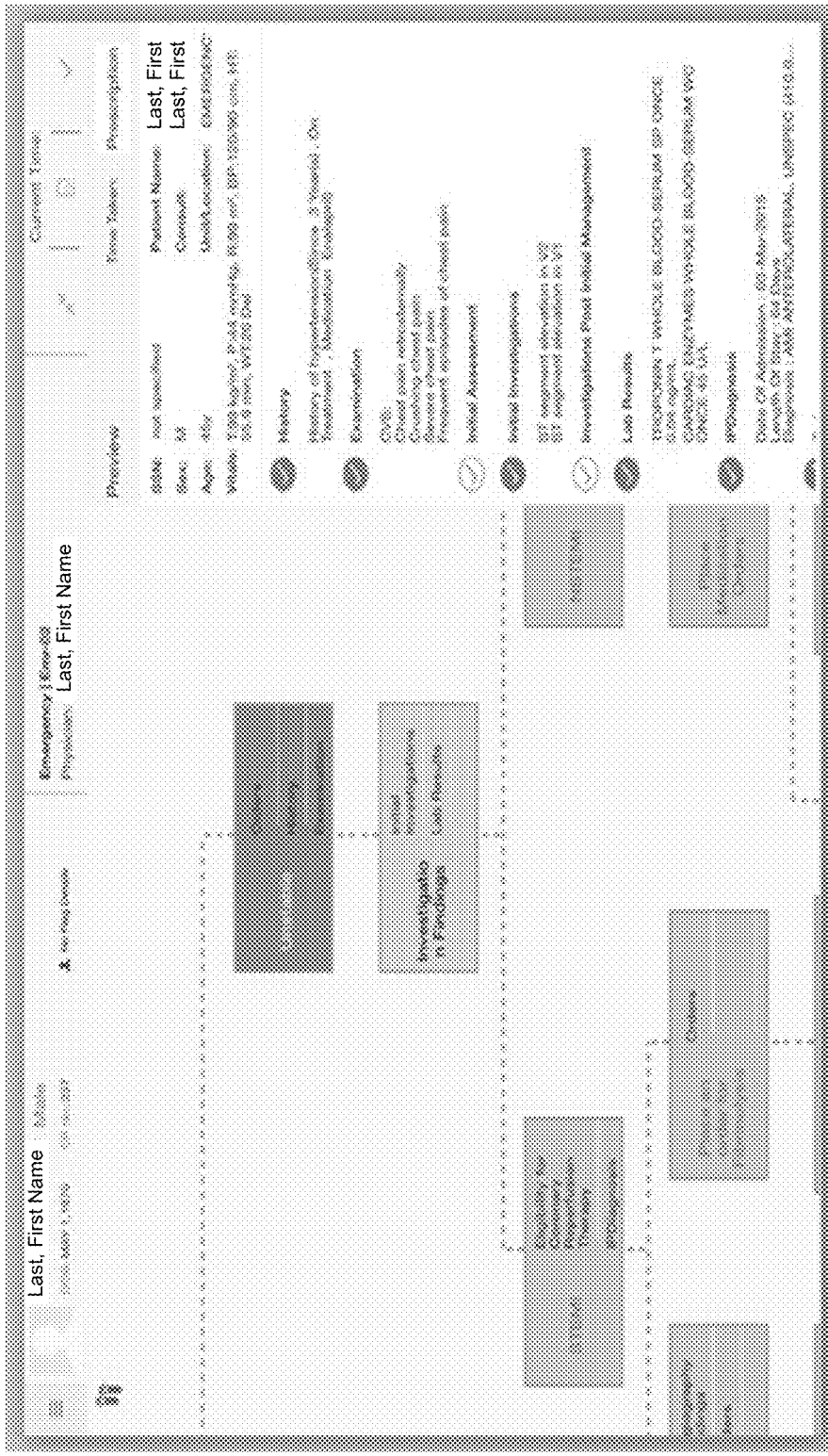

For each complaint and/or symptom that is associated with a patient standard of care, mobile device 109 may, at step 906, enforce the patient standard of care. As discussed above, a patient standard of care may be a preset ordered checklist or tree of tasks to be performed by the physician. As a result, mobile device 109 may only permit inputs from the physician relating to the complaint or symptom in a specific order. As an example, the complaint may be chest pain, which may be associated with the patient standard of care shown in FIGS. 10-17. As shown in these figures, the patient standard of care for chest pain may be the following ordered tree: verify if unstable, investigation and findings, stemi or nstemi, etc. If nstemi, then physician may place an order to an angiograph or fibrinolysis, etc. In instances where the patient standard of care is an ordered tree, separate branches may represent alternative routes of tasks or input to be completed before proceeding further down the branch. Mobile device 109 may display the ordered tree and, in response to receiving the physician's selection of a node (e.g., task) of the tree, mobile device 109 may display a pop-up window of detailed information to be filled out by the physician to complete that task. As an example, in response to receiving a user selection of the unstable node, an actionable pop-up window may be displayed as shown in FIG. 12, which may display multiple options to be selected by the physician. In some instances, the ordered checklist and/or tree might not follow ordered steps set out in a subjective, objective assessment plan (SOAP) methodology.

Mobile device 109 may prevent and/or otherwise block the physician from the entering input out-of-order. As an example, the physician might not be able to place an order for fibrinolysis until the unstable, investigation of findings and stemi tasks have been completed.

For each complaint and/or diagnosis that might not be associated with a patient standard of care, the physician may, at step 908, submit inputs relating to treating the complaint or symptom (e.g., the patient's chest pain) in any order. Mobile device 109 may permit the physician to enter inputs in an order different from an order provided by SOAP.

In one or more arrangements, one or more medical professional may author a note for a patient on a periodic basis (e.g., daily, weekly, and/or yearly), which they may submit using natural language input (e.g., free text) via a user-friendly medical app installed on mobile device 109. The natural language inputs may include patient assessment, initial diagnosis, etc. Data may be captured from the natural language by either the user-friendly medical app itself or backend services 215 that received the note from the user-friendly medical app. The data may be captured by populating disease-specific templates (stored at the portable device and/or a backend service).

In some instances, backend services 215 may receive notes for a particular patient from multiple mobile devices. In such instances, backend services 215 may aggregate the note into one aggregating note for example by appending each note associated with the patient to one another. Further, backend services 215 may transmit the aggregated note to each of the mobile devices for view and additional edits by the medical professionals.

At the end of the particular time period (e.g., at the end of each day, month and/or year) a medical professional responsible for the patient's care may edit and sign the note (e.g., the aggregated note) on behalf of the one or more medical professionals to thereby lock the note. Once locked, the note may not be altered. For instance, the user-friendly medical app and/or backend services 215 may prevent other users from modifying the note. Use of this note taking feature of the user-friendly medical app may eliminate redundant statements and miscommunications among the one or more professionals. Additionally, once the note is signed, the user friendly medical app and/or backend services 215 may codify the data of the note into one or more clinical codes representative of clinical terminology (e.g., Systematized Nomenclature of Medicine—Clinical Terms).

Further, the user-friendly medical app and/or backend services 215 may store a mapping of the clinical codes to one or more suggested billing codes (e.g., ICD-10 billing codes) and use the mapping to identify suggested billing codes based on the clinical codes. Using a rules engine, the user-friendly medical app itself and/or the backend services may cause the user-friendly medical app to display requests for additional information to justify one or more of the billing codes based on one or more rule of the rules engine. The rules ensure that there is sufficient information to justify a particular billing code by determining whether the data captured is sufficient to populate a set of fields associated with a billing code. The justification may include diagnoses and/or treatment of the patient. As a result of use of the mapping, medical professionals may focus their attention on clinical codes rather than on billing codes.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A system comprising:
a backend computing device configured to store one or more physician-specific preferences; and
a mobile device communicatively coupled to the backend computing device and an electronic health record information system, the mobile device comprising a processor, a screen, and a computer-readable medium,
the computer-readable medium storing instructions that, when executed by the processor, cause the mobile device to permit a first physician to operate in a non-linear and non-sequential order by:
dynamically reordering, by the backend computing device, tiles in a tile-based user interface, wherein the tile-based user interface is reordered to be unified and streamlined into a single screen, wherein the tile-based user interface is customized for the first physician based on the one or more physician-specific preferences and the first physician's treatment history of patients, wherein the tile-based user interface comprises, for a patient, a documentation tile, a diagnosis tile, a treatment plan tile, a lab results tile, a medication or prescription tile, and a significant information icon;
displaying, on the screen of the mobile device, the reordered tiles of the tile-based user interface;
monitoring, using one or more timestamps, how long the reordered tiles are displayed on the tile-based user interface before receiving physician input;
receiving a touch-based gesture on the screen of the mobile device from among a plurality of touch-based gestures, wherein the plurality of touch-based gestures are associated with different actions based on which tiles are displayed on the tile-based user interface when the touch-based gesture is performed, wherein the touch-based gesture is a swipe-left user gesture with two fingers;
in response to the receiving the swipe-left user gesture, performing a copy-patient-information action when a first tile is displayed, but performing a copy-medications action when a second tile is displayed;
receiving a user selection to activate the significant information icon; and
displaying abnormal lab results of the patient that are significant for the first physician based on a task to be performed by the first physician, wherein the abnormal lab results are not significant to a second physician to perform a different task on the patient.

2. The system of claim 1,
wherein the computer-readable medium storing instructions that, when executed by the processor, cause the mobile device to:
remove, from the tile-based user interface, abnormal lab results that are not significant to the task to be performed by the first physician.

3. The system of claim 1,
wherein the computer-readable medium storing instructions that, when executed by the processor, cause the mobile device to:
remove, from the tile-based user interface, normal lab results.

4. The system of claim 1,
wherein the computer-readable medium storing instructions that, when executed by the processor, cause the mobile device to:
receive input from the first physician; and
dynamically reorder the tile-based user interface based on the input.

5. The system of claim 1,
wherein the computer-readable medium storing instructions that, when executed by the processor, cause the mobile device to:
receive input from the first physician indicative of a first diagnosis of the patient;
determine that the first diagnosis is associated with a patient standard of care specifying an order of user inputs;
permit further inputs from the first physician that are in accordance with the patient standard of care specifying the order of user inputs; and
block other inputs from the first physician that are not in accordance with the patient standard of care specifying the order of user inputs.

6. The system of claim 1,
wherein the computer-readable medium storing instructions that, when executed by the processor, cause the mobile device to:
receive, from the first physician, one or more conditions of the patient for triggering an alert and one or more specified persons to send an alert message;
determine that the one or more conditions for triggering the alert are satisfied; and
send the alert message to the one or more specified persons, the alert message comprising an identification of a diagnosis for the one or more specified persons to prevent from occurring.

7. The system of claim 1, wherein the backend computing device is configured to intercept communications between the mobile device and the electronic health record information system and modify content of the communications based on the one or more physician-specific preferences.

8. The system of claim 7, wherein a modification of the content is based on a range of acceptable values for a demographic customized by the first physician.

9. An apparatus comprising:
a processor; and
a computer-readable memory coupled to the processor, the computer-readable memory storing instructions that, when executed by the processor, cause the apparatus to:
display a tile-based user interface customized for a first physician, wherein one or more physician-specific preferences are stored on a backend computing device;
retrieve the one or more physician-specific preferences to determine the tile-based user interface customized for the first physician;
receive input from the first physician indicative of a first diagnosis of a patient, wherein the input is a touch-based gesture from among a plurality of touch-based gestures, wherein the plurality of touch-based gestures are associated with different actions based on which tiles are displayed on the tile-based user interface when the touch-based gesture is performed, wherein the touch-based gesture is a swipe-left user gesture with two fingers;
in response to the receiving the swipe-left user gesture, perform a copy-patient-information action when a first tile is displayed, but perform a copy-medications action when a second tile is displayed;
determine that the first diagnosis is associated with a patient standard of care specifying an order of user inputs;
permit further inputs from the first physician that are in accordance with the patient standard of care specifying the order of user inputs;
monitor, using one or more timestamps, how long the tile-based user interface customized for the first physician is displayed before receiving the first physician's input;
block other inputs from the first physician that are not in accordance with the patient standard of care specifying the order of user inputs; and
dynamically reorder, by the backend computing device, the tile-based user interface based on at least one user input.

10. The apparatus of claim 9, wherein the computer-readable memory stores instructions that, when executed by the processor, cause the apparatus to:
receive a user selection to activate a significant information icon of the tile-based user interface; and
display abnormal lab results of the patient that are significant for the first physician based on a task to be performed by the first physician, wherein the abnormal lab results are not significant to a second physician to perform a different task.

11. The apparatus of claim 10, wherein the computer-readable memory stores instructions that, when executed by the processor, cause the apparatus to:
remove, from the tile-based user interface, abnormal lab results of the patient that are not significant to the task to be performed by the first physician.

12. The apparatus of claim 10, wherein the computer-readable memory stores instructions that, when executed by the processor, cause the apparatus to:
determine that a value associated with the patient is abnormal based on a range of acceptable values for a demographic customized by the first physician.

13. The apparatus of claim 9, wherein the tile-based user interface comprises, for the patient, a documentation tile, a diagnosis tile, a treatment plan tile, a lab results tile, and a medication or prescription tile.

14. A method involving enhancing a tile-based user interface on a mobile device by operating it in a distributed fashion with a backend server, the method comprising:
dynamically reordering, by the backend server communicatively coupled to the mobile device, tiles in a tile-based user interface, wherein the tile-based user interface is reordered to be unified and streamlined into a single screen to permit a first physician to operate in a non-linear and non-sequential order, wherein the tile-based user interface is customized for the first physician based on one or more physician-specific preferences and the first physician's treatment history of patients, wherein the tile-based user interface comprises, for a patient, a documentation tile, a diagnosis tile, a treatment plan tile, a lab results tile, a medication or prescription tile, and a significant information icon;

displaying, by a processor of the mobile device, on a display screen of the mobile device, the reordered tiles of the tile-based user interface;

receiving a touch-based gesture on the display screen of the mobile device from among a plurality of touch-based gestures, wherein the plurality of touch-based gestures are associated with different actions based on which tiles are displayed on the tile-based user interface when the touch-based gesture is performed, wherein the touch-based gesture is a swipe-left user gesture with two fingers;

in response to the receiving the swipe-left user gesture, performing, by the mobile device, a copy-patient-information action when a first tile is displayed, but performing a copy-medications action when a second tile is displayed;

receiving, by the mobile device, a user selection to activate the significant information icon; and displaying, by the mobile device, abnormal lab results of the patient that are significant for the first physician based on a task to be performed by the first physician, wherein the abnormal lab results are not significant to a second physician to perform a different task on the patient.

15. The method of claim 14, further comprising:
after the receiving, removing, from the tile-based user interface, abnormal lab results that are not significant to the task to be performed by the first physician.

16. The method of claim 14, further comprising:
after the receiving, removing, from the tile-based user interface, normal lab results.

17. The method of claim 16, further comprising:
determining whether a lab result is normal based on a range of acceptable values for a demographic customized by the first physician.

18. The method of claim 14, further comprising:
receiving input from the first physician; and
dynamically reordering the tile-based user interface based on the input.

19. The method of claim 14, further comprising:
receiving input from the first physician indicative of a first diagnosis of the patient;
determining that the first diagnosis is associated with a patient standard of care specifying an order of user inputs;
permitting further inputs from the first physician that are in accordance with the patient standard of care specifying the order of user inputs; and
blocking other inputs from the first physician that are not in accordance with the patient standard of care specifying the order of user inputs.

* * * * *